(12) United States Patent
Kim

(10) Patent No.: US 10,676,507 B2
(45) Date of Patent: Jun. 9, 2020

(54) PEPTIDE AND COMPOSITION CONTAINING THE SAME FOR ANTI-INFLAMMATION, ANTI-FIBROSIS, WOUND HEALING, AND ANTICANCER TREATMENT

(71) Applicants: GemVax & KAEL CO., LTD., Daejeon (KR); Sang Jae Kim, Seoul (KR)

(72) Inventor: Sang Jae Kim, Seoul (KR)

(73) Assignee: GEMVAX & KAEL CO., LTD., Daejeon (KR)

( * ) Notice: Subject to any disclaimer, the term of this patent is extended or adjusted under 35 U.S.C. 154(b) by 0 days.

(21) Appl. No.: 15/576,111

(22) PCT Filed: May 25, 2016

(86) PCT No.: PCT/KR2016/005529
§ 371 (c)(1),
(2) Date: Nov. 21, 2017

(87) PCT Pub. No.: WO2016/190660
PCT Pub. Date: Dec. 1, 2016

(65) Prior Publication Data
US 2018/0134749 A1    May 17, 2018

(30) Foreign Application Priority Data

May 26, 2015   (KR) ........................ 10-2015-0073188

(51) Int. Cl.
| | | |
|---|---|---|
| *A61K 38/08* | (2019.01) |
| *A61K 38/10* | (2006.01) |
| *A61K 38/00* | (2006.01) |
| *C07K 7/06* | (2006.01) |
| *C07K 7/08* | (2006.01) |
| *C07K 7/00* | (2006.01) |
| *C07K 14/00* | (2006.01) |
| *A61P 29/00* | (2006.01) |
| *A61P 17/02* | (2006.01) |
| *A61P 17/06* | (2006.01) |
| *A61P 17/00* | (2006.01) |
| *A61P 19/02* | (2006.01) |
| *A61P 1/00* | (2006.01) |
| *A61P 1/04* | (2006.01) |
| *A61P 1/16* | (2006.01) |
| *A61P 25/00* | (2006.01) |
| *A61P 35/00* | (2006.01) |
| *A61P 37/00* | (2006.01) |
| *A61P 3/10* | (2006.01) |
| *A61P 19/00* | (2006.01) |
| *A61P 11/00* | (2006.01) |

(52) U.S. Cl.
CPC ...... *C07K 7/06* (2013.01); *A61P 1/00* (2018.01);
*A61P 1/04* (2018.01); *A61P 1/16* (2018.01);
*A61P 3/10* (2018.01); *A61P 11/00* (2018.01);
*A61P 17/00* (2018.01); *A61P 17/02* (2018.01);
*A61P 17/06* (2018.01); *A61P 19/00* (2018.01);
*A61P 19/02* (2018.01); *A61P 25/00* (2018.01);
*A61P 29/00* (2018.01); *A61P 35/00* (2018.01);
*A61P 37/00* (2018.01); *A61K 38/00* (2013.01)

(58) Field of Classification Search
CPC ........ A61K 38/00; A61K 38/08; A61K 38/10; C07K 7/06; C07K 7/00; C07K 7/08; C07K 14/00; A61P 11/00; A61P 17/00; A61P 17/02; A61P 17/06; A61P 19/02; A61P 1/00; A61P 1/04; A61P 1/16; A61P 25/00; A61P 29/00; A61P 35/00; A61P 37/00; A61P 3/10
USPC ........... 514/17.2, 9.4, 21.2, 21.3, 21.4, 21.5, 514/21.6, 21.7; 530/300, 324, 325, 326, 530/327, 328, 329, 330
See application file for complete search history.

(56) References Cited

U.S. PATENT DOCUMENTS

| | | | | |
|---|---|---|---|---|
| 7,041,814 B1 * | 5/2006 | Weinstock | ........... | C07K 14/265 435/252.3 |
| 7,745,391 B2 * | 6/2010 | Mintz | ..................... | G06F 19/24 514/19.3 |
| 8,252,282 B2 | 8/2012 | Santos | | |
| 9,023,987 B2 | 5/2015 | Chung et al. | | |
| (Continued) | | | | |

FOREIGN PATENT DOCUMENTS

| | | | |
|---|---|---|---|
| JP | 2010252810 A | 11/2010 |
| KR | 19980703610 A | 12/1998 |
| (Continued) | | | |

OTHER PUBLICATIONS

UniProt A0A1Z5TE24, pp. 1-4. Integrated into UniProtKB/TrEMBL Sep. 27, 2017.*

(Continued)

*Primary Examiner* — Julie Ha
(74) *Attorney, Agent, or Firm* — Sterne, Kessler, Goldstein & Fox P.L.L.C.

(57) ABSTRACT

Peptides and compositions comprising the peptides, and more particularly, a peptide effective in anti-inflammation, anti-fibrosis, wound healing, and anti-cancer treatment, and a composition including the same are described. The peptides provided herein and the compositions comprising the peptides exhibit an effect of alleviating, preventing, or treating inflammation, fibrosis, wounds, and symptoms of diseases such as cancer including these symptoms, and thus may provide a method of preventing or treating associated diseases.

16 Claims, 8 Drawing Sheets
Specification includes a Sequence Listing.

(56) References Cited

U.S. PATENT DOCUMENTS

| | | | |
|---|---|---|---|
| 9,029,636 B2 * | 5/2015 | Wu | C07K 14/415 800/285 |
| 9,527,888 B2 | 12/2016 | Kim et al. | |
| 9,572,900 B2 | 2/2017 | Kim | |
| 9,631,184 B2 | 4/2017 | Kim | |
| 9,757,473 B2 | 9/2017 | Kim | |
| 9,902,945 B2 | 2/2018 | Kim et al. | |
| 2004/0210036 A1 | 10/2004 | Dwyer et al. | |
| 2006/0106196 A1 | 5/2006 | Gaudernack et al. | |
| 2009/0186802 A1 | 7/2009 | Alluis et al. | |
| 2011/0318380 A1 | 12/2011 | Brix et al. | |
| 2012/0065124 A1 | 3/2012 | Morishita et al. | |
| 2013/0330335 A1 * | 12/2013 | Bremel | G16B 20/00 424/134.1 |
| 2013/0333061 A1 * | 12/2013 | Wu | C07K 14/415 800/260 |
| 2015/0099693 A1 | 4/2015 | Kim et al. | |
| 2015/0125438 A1 | 5/2015 | Kim et al. | |
| 2015/0307859 A1 | 10/2015 | Kim | |
| 2015/0343095 A1 | 12/2015 | Kim | |
| 2016/0002613 A1 | 1/2016 | Kim | |
| 2016/0120966 A1 | 5/2016 | Kim | |
| 2016/0151512 A1 | 6/2016 | Kim | |
| 2017/0081376 A1 | 3/2017 | Kim et al. | |
| 2017/0112941 A1 | 4/2017 | Panitch et al. | |
| 2017/0112942 A1 | 4/2017 | Kim | |
| 2017/0275603 A1 | 9/2017 | Kim et al. | |
| 2018/0134749 A1 | 5/2018 | Kim | |

FOREIGN PATENT DOCUMENTS

| | | | | |
|---|---|---|---|---|
| KR | 20060036382 A | 4/2006 | | |
| KR | 20070083218 A | 8/2007 | | |
| KR | 20090103957 A | 10/2009 | | |
| KR | 20100085527 A | 7/2010 | | |
| KR | 20100118122 A | 11/2010 | | |
| KR | 20110060940 A | 6/2011 | | |
| KR | 20110093899 A | 8/2011 | | |
| KR | 20110130943 A | 12/2011 | | |
| KR | 20120026408 A | 3/2012 | | |
| KR | 20140005110 A | 1/2014 | | |
| KR | 10-2014-0089295 B1 | 3/2020 | | |
| WO | WO-2010012850 A1 | 2/2010 | | |
| WO | WO-2011101173 A1 | 8/2011 | | |
| WO | WO-2011150494 A1 | 12/2011 | | |
| WO | WO 2013/167574 A1 | 11/2013 | | |
| WO | WO 2013/167298 A1 | 11/2016 | | |
| WO | WO-2016190660 | 12/2016 | | |
| WO | WO-2017116138 A1 * | 7/2017 | | A61K 38/08 |

OTHER PUBLICATIONS

UniProt K7LHP1, pp. 1-3. Integrated into UniProtKB/TrEMBL Jan. 9, 2013.*
WO2017116138 Machine translation, Jul. 2017. (Year: 2017).*
UniProt H3H2V1, pp. 1-5. Integrated into UniProtKB/TrEMBL Apr. 18, 2012. (Year: 2012).*
Peasron WR, "An Introduction to Sequence Similarity ("Homology") Searching", Curr. Protoc. Bioinform., 42: 3.1.1-3.1.8. (Year: 2013).*
Kanduc D, "Homology, similarity, and identity in peptide epitope innunodefinition", J. Pept. Sci., 18: 487-494. (Year: 2012).*
Berendsen, H.J., "A Glimpse of the Holy Grail?," Science 282(5389):642-643, American Association for the Advancement of Science, United States (1998).
Bradley, C.M. and Barrick, D., "Limits of Cooperativity in a Structurally Modular Protein: Response of the Notch Ankyrin Domain to Analogous Alanine Substitutions in Each Repeat," Journal of Molecular Biology 324(2):373-386, Elsevier, England (2002).
Cho, Y.J., "GemVax & Kael (082270)," Hana Daetoo Securities, Company Report, Sep. 10, 2012, 9 pages.
Du, C., et al., "Conformational and Topological Requirements of Cell-permeable Peptide Function," The Journal of Peptide Research 51(3):235-243, Munksgaard, Denmark (1998).
Fire, A., et al., "Potent and Specific Genetic Interference by Double-stranded RNA in Caenorhabditis Elegans," Nature 391(6669):806-811, Nature Publishing Group, England (1998).
Fittipaldi, A., et al., "Cell Membrane Lipid Rafts Mediate Caveolar Endocytosis of HIV-1 Tat Fusion Proteins," Journal of Biological Chemistry 278(36): 34141-34149, American Society for Biochemistry and Molecular Biology, United States (2003).
Fonseca, S.B., et al., "Recent Advances in the Use of Cell-Penetrating Peptides for Medical and Biological Applications," Advanced Drug Delivery Reviews 61(11):953-964, Elsevier Science Publishers, Netherlands (2009).
Ge, D. and Levicky, R., "A Comparison of Five Bioconjugatable Ferrocenes for Labeling of Biomolecules," Chemical Communications 46(38):7190-7192, Royal Society of Chemistry, England (2010).
Harvard School of Public Health, "Obesity Causes," Accessed at http://www.hsph.harvard.edu/obesity-prevention-source/obesity-causes/ accessed on Oct. 6, 2014, 3 pages.
Heitz, F., et al., "Twenty Years of Cell-Penetrating Peptides: From Molecular Mechanisms to Therapeutics," British Journal of Pharmacology 157(2):195-206, Wiley, England (2009).
International Preliminary Report on Patentability for International Application No. PCT/KR2013/008438, The International Bureau of WIPO, Switzerland, dated Mar. 24, 2015, 10 pages.
International Preliminary Report on Patentability for International Application No. PCT/KR2013/008445, The International Bureau of WIPO, Switzerland, dated Mar. 24, 2015, 13 pages.
International Search Report for International Application No. PCT/KR2013/006218, Korean Intellectual Property Office, Republic of Korea, dated Sep. 26, 2013, 8 pages.
International Search Report for International Application No. PCT/KR2013/008438, Korean Intellectual Property Office, Republic of Korea, dated Dec. 23, 2013, 8 pages.
International Search Report for International Application No. PCT/KR2013/008445, Korean Intellectual Property Office, Republic of Korea, dated Dec. 23, 2013, 10 pages.
International Search Report for International Application No. PCT/KR2013/008459, Korean Intellectual Property Office, Republic of Korea, dated Dec. 23, 2013, 8 pages.
Kalnins, A., et al., "Sequence of the Lacz Gene of *Escherichia Coli*," The EMBO Journal 2(4):593-597, Wiley Blackwell, England (1983).
Lee, S.A., et al., "Heat Shock Protein-Mediated Cell Penetration and Cytosolic Delivery of Macromolecules by a Telomerase-Derived Peptide Vaccine," Biomaterials 34(30):7495-7505, Elsevier Science, Netherlands (2013).
Luft, R., et al., "A Case of Severe Hypermetabolism of Nonthyroid Origin with a Defect in the Maintenance of Mitochondrial Respiratory Control: A Correlated Clinical, Biochemical, and Morphological Study," Journal of Clinical Investigation 41:1776-1804, American Society for Clinical Investigation, United States (1962).
Merck, "Obesity, The Merck Manual Professional Edition," accessed at https://www.merckmanuals.com/professional/nutritional-disorders/obesity-and-the-metabolic-syndrome/obesity, accessed on Oct. 6, 2014, 9 pages.
Modica-Napolitano, J.S. and Singh, K.K., "Mitochondria as Targets for Detection and Treatment of Cancer," Expert Reviews in Molecular Medicine 4(9):1-19, Cambridge University Press, England (2002).
National Heart, Lung and Blood Institute, "What Causes Overweight and Obesity?" accessed at http://www.nhlbi.nih.gov/health/health-topics/topics/obe/causes.html, accessed on Oct. 6, 2014, 5 pages.
Ngo. et al., "Computational Complexity, Protein Structure Prediction, and the Levinthal Paradox," in The Protein Folding Problem and Tertiary Structure Prediction, Merz, Jr., K.M., and Le Grand, S.M., eds., pp. 491-494, Birkhauser Boston, United States (1994).
Novina, C.D. and Sharp, P.A., "The RNAi Revolution," Nature 430(6996):161-164, Nature Publishing Group, England (2004).
Rana, T.M., "Illuminating the Silence: Understanding the Structure and Function of Small RNAs," Nature Reviews. Molecular Cell Biology 8(1):23-36, Nature Publishing Group, England (2007).

(56) References Cited

OTHER PUBLICATIONS

Rudinger, J., "Characteristics of the Amino Acids as Components of a Peptide Hormone Sequence," in Peptide Hormones, Parsons, J.A., ed., University Park Press, United States (1976).
Schwarze, S.R., et al., "In Vivo Protein Transduction: Delivery of a Biologically Active Protein Into the Mouse," Science 285(5433):1569-1572, American Association for the Advancement of Science, United States (1999).
SIGMA Genosys, "Designing Custom Peptides," accessed at http://www.sigma-genosys.com/peptide_design.asp, Accessed on Dec. 16, 2004, 2 pages.
Smith, D.B. and Johnson, K.S., "Single-step Purification of Polypeptides Expressed in *Escherichia Coli* as Fusions with Glutathione S-transferase," Gene 67(1):31-40, Elsevier, Netherlands (1988).
Tomari Y. and Zamore, P.D., "Perspective: Machines for RNAi," Genes and Development 19(5):517-529, Cold Spring Harbor Laboratory Press, United States (2005).
Voet, D. and Voet, J.G., "Abnormal Hemoglobins," in Biochemistry, 2nd Edition, Chapter 9, pp. 235-241, John Wiley & Sons, Inc., United States (1995).
Written Opinion for International Application No. PCT/KR2013/006218, Korean Intellectual Property Office, Republic of Korea, dated Sep. 26, 2013, 26 pages.
Written Opinion for International Application No. PCT/KR2013/008438, Korean Intellectual Property Office, Republic of Korea, dated Dec. 23, 2013, 9 pages.
Written Opinion for International Application No. PCT/KR2013/008445, Korean Intellectual Property Office, Republic of Korea, dated Dec. 23, 2013, 12 pages.
Written Opinion for International Application No. PCT/KR2013/008459, Korean Intellectual Property Office, Republic of Korea, dated Dec. 23, 2013, 9 pages.
Cho, Y.J., "A Godsend About to Arrive," GemVax (082270), Hana Daetoo Securities Co., Ltd., Company Report, 8 pages (Sep. 10, 2012).
Fonesca, S.B., et al., "Recent advances in the use of cell-penetrating peptides for medical and biological applications," *Adv. Drug Deliv. Rev.* 61:953-964, Elsevier B.V., Netherlands (2009).
Santos, J.H., et al., "Mitochondrial hTERT exacerbates free-radical-mediated mtDNA damage," *Aging Cell*, 3, pp. 399-411, Blackwell Publishing Ltd/ Anatomical Society of Great Britain and Ireland, England and Ireland (Jul. 29, 2004).
Horwich et al., "A leader peptide is sufficient to direct mitochondrial import of a chimeric protein," EMBO J. 4(5): 1129-1135, United Kingdom (1985).
Armstrong, "Mitochondrial Medicine: Pharmacological Targeting of Mitochondria in Disease," British Journal of Pharmacology, 151: 1154-1165 United Kingdom (2007).
Lopez et al., Mitochondria-targeted Nitroxides as MRI Contrast Agents and Chemotherapeutics, Free Radical Biology & Medicine, 45 (Suppl. 1): S55 (2008).
Salaklang et al. "Superparamagnetic nanoparticles as a power systems biology characterization tool in the physiological context," Angewandte Chemie Int. Ed. 47:7857-7860 (2008).
International Search Report and Written Opinion for International Application No. PCT/KR2016/005529, Korean Intellectual Property Office, Republic of Korea, dated Aug. 18, 2016, 13 pages.

* cited by examiner

[Fig. 1]
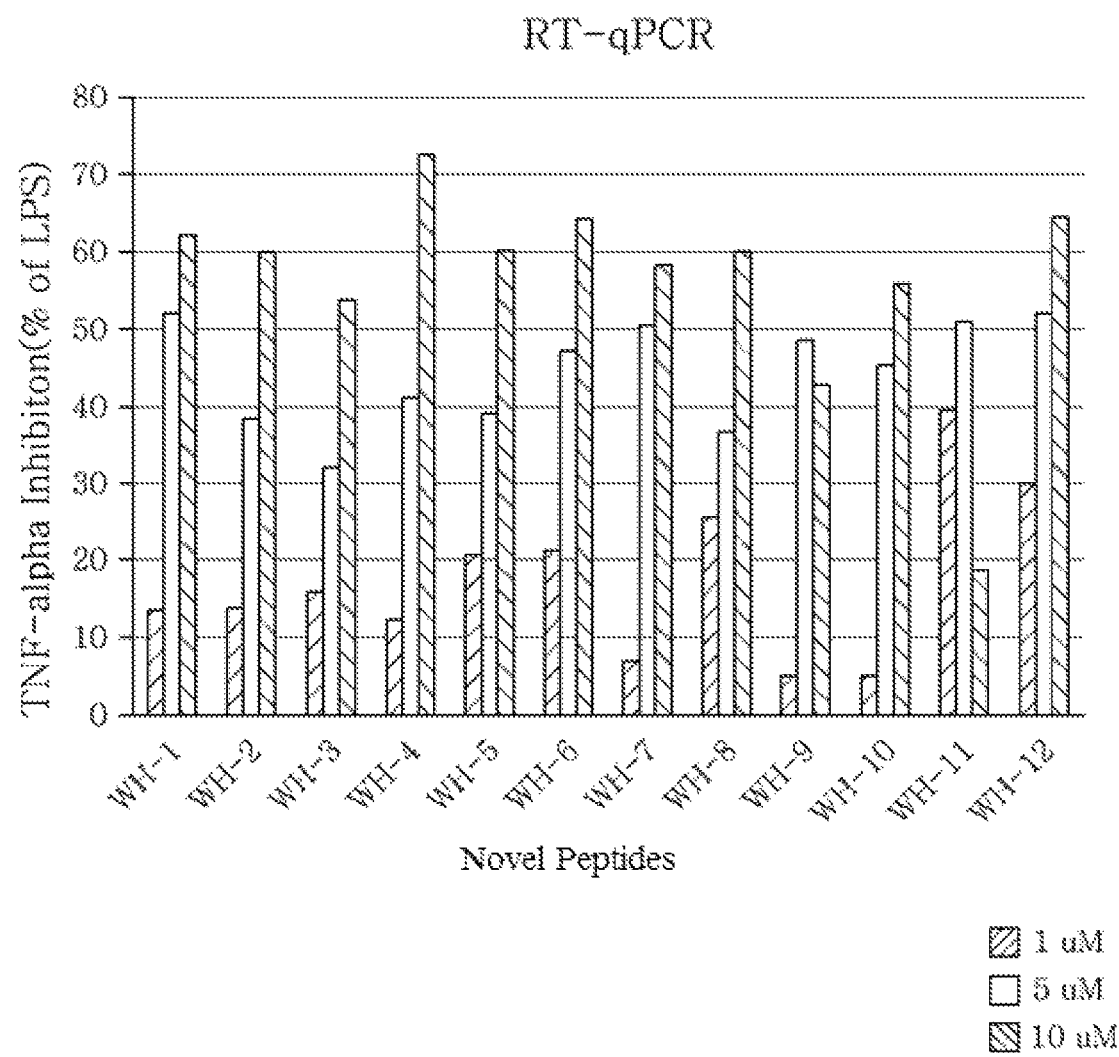

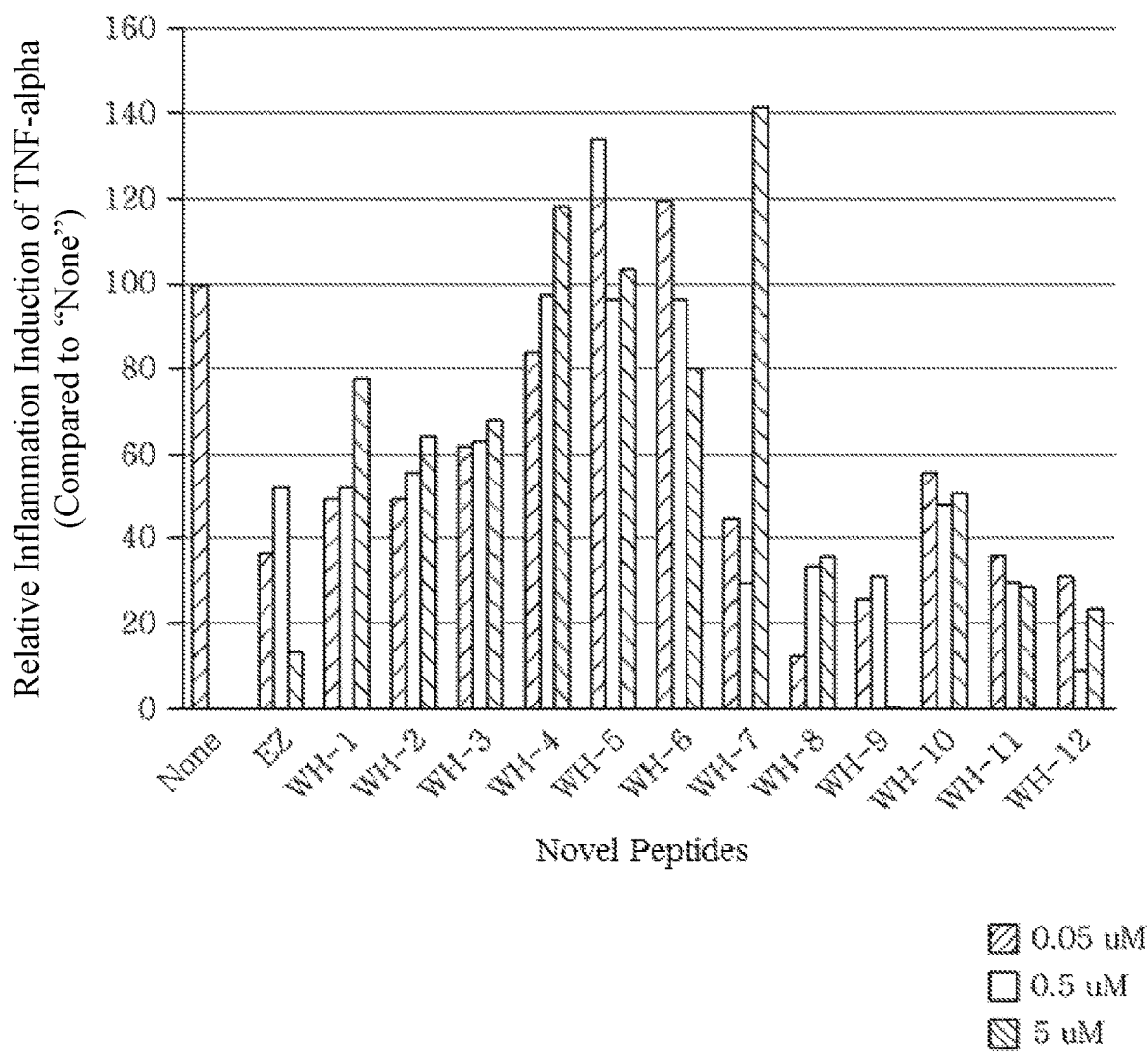
[Fig. 2]

[Fig. 3]
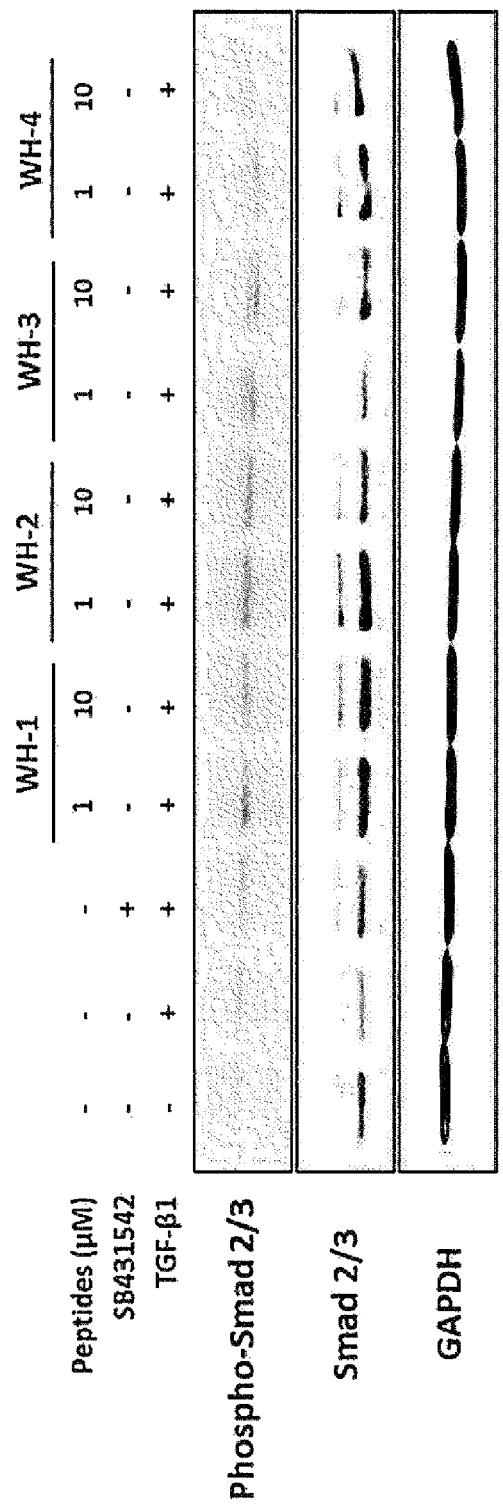
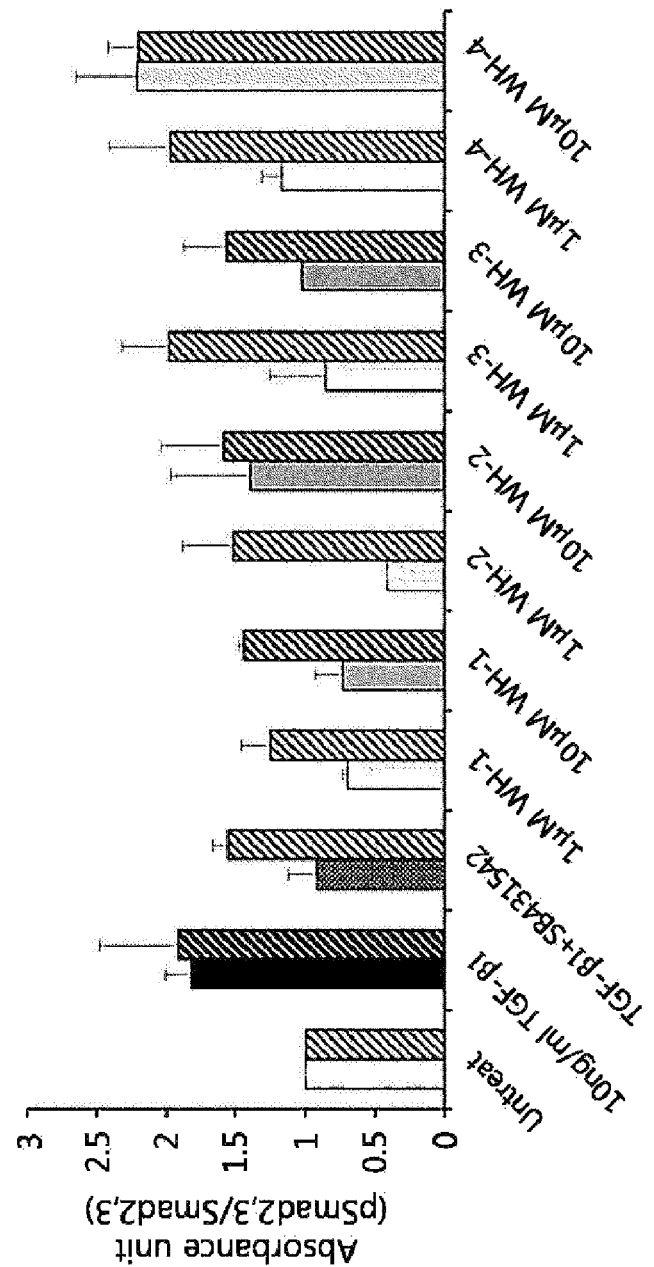

[Fig. 4]
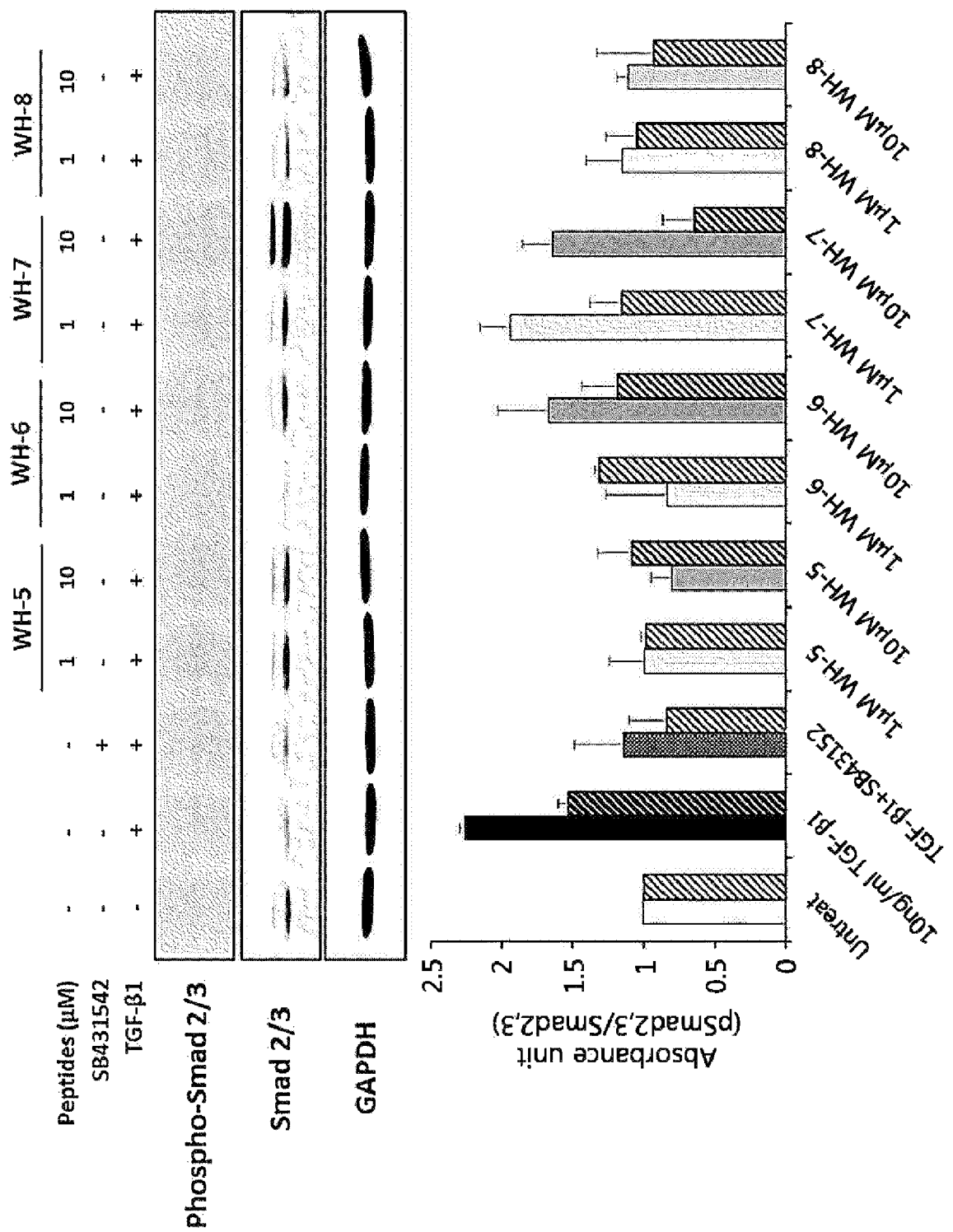

[Fig. 5]
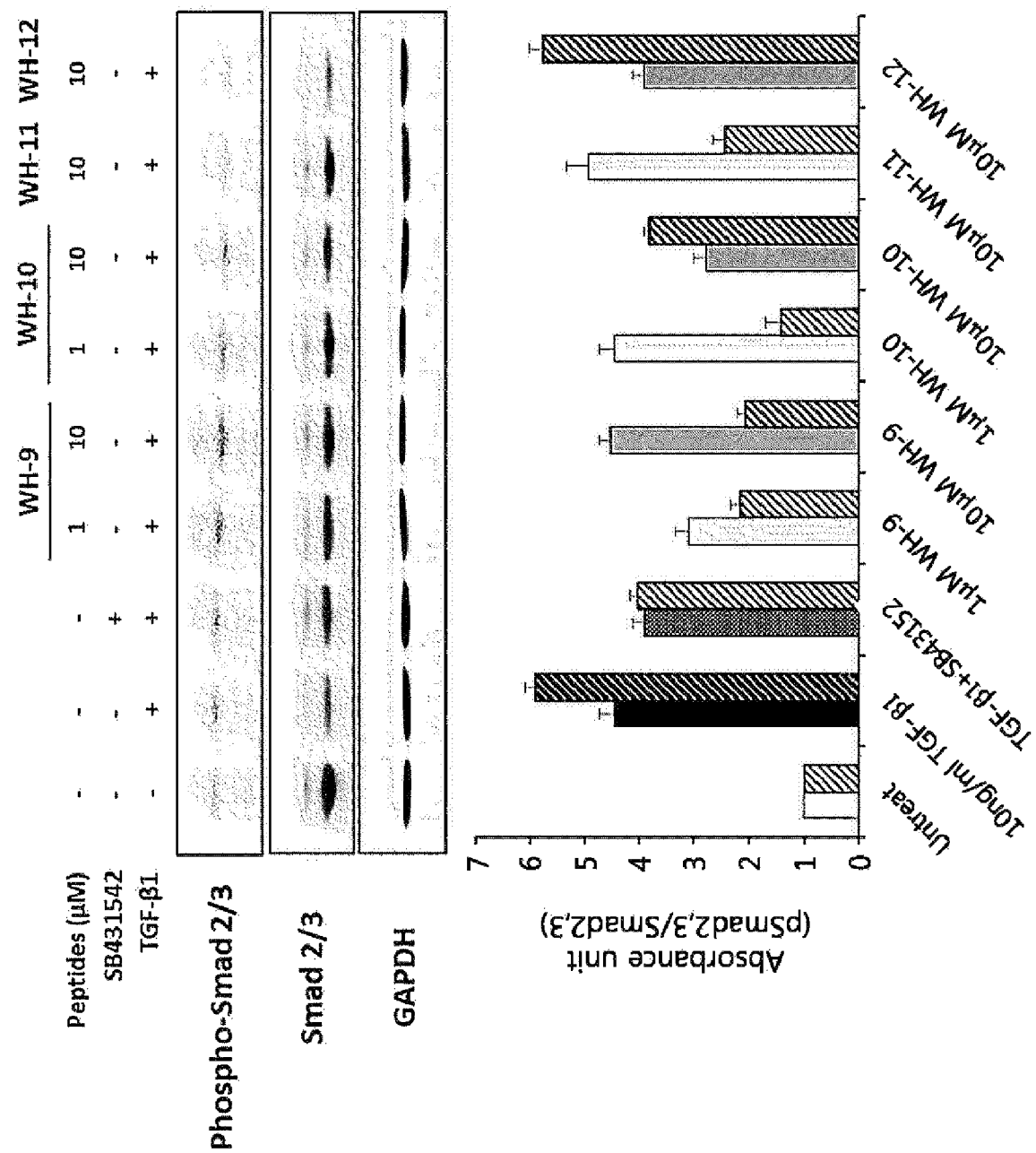

【Fig. 6】
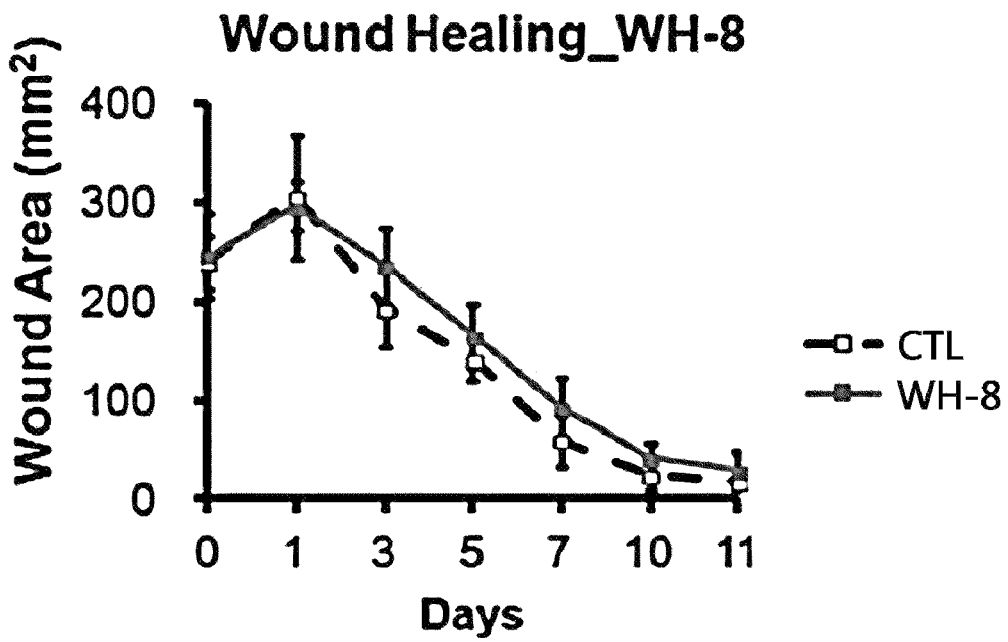
【Fig 7】
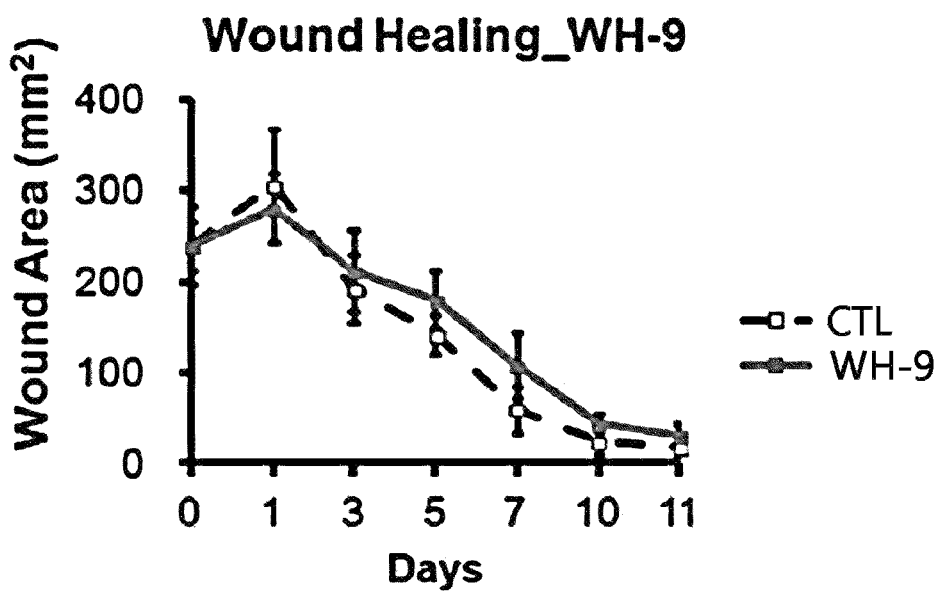

【Fig. 8】
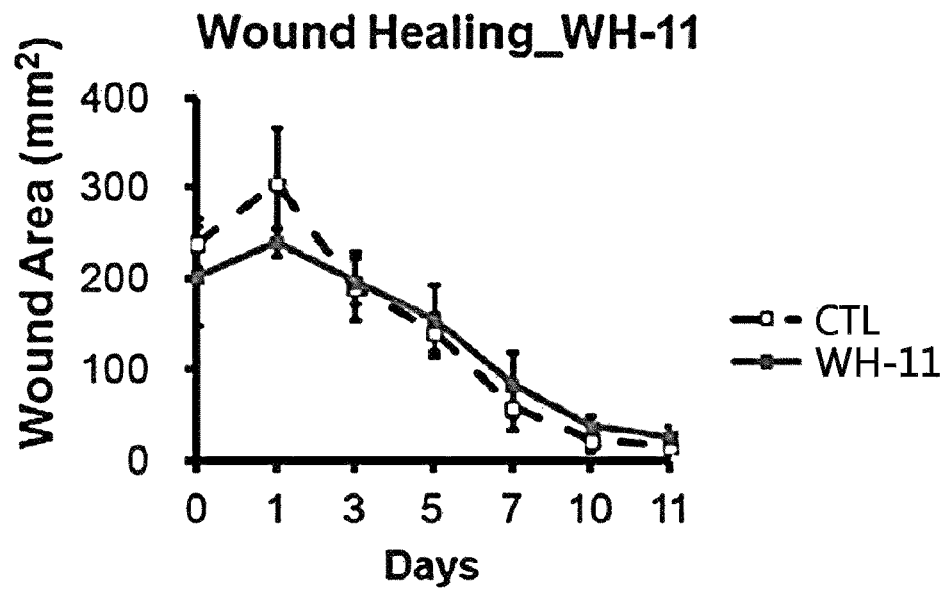
【Fig. 9】
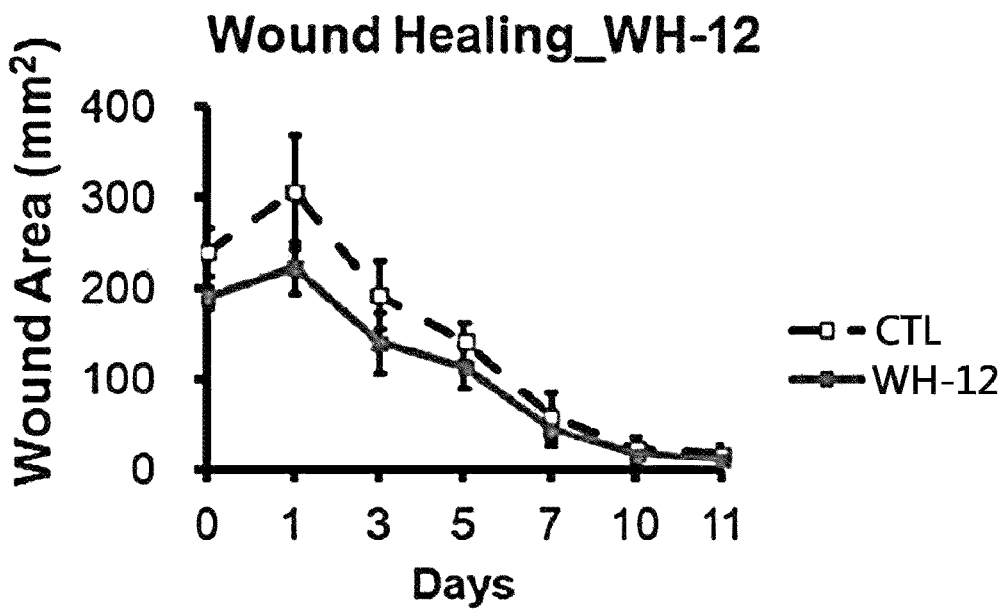

[Fig. 10]
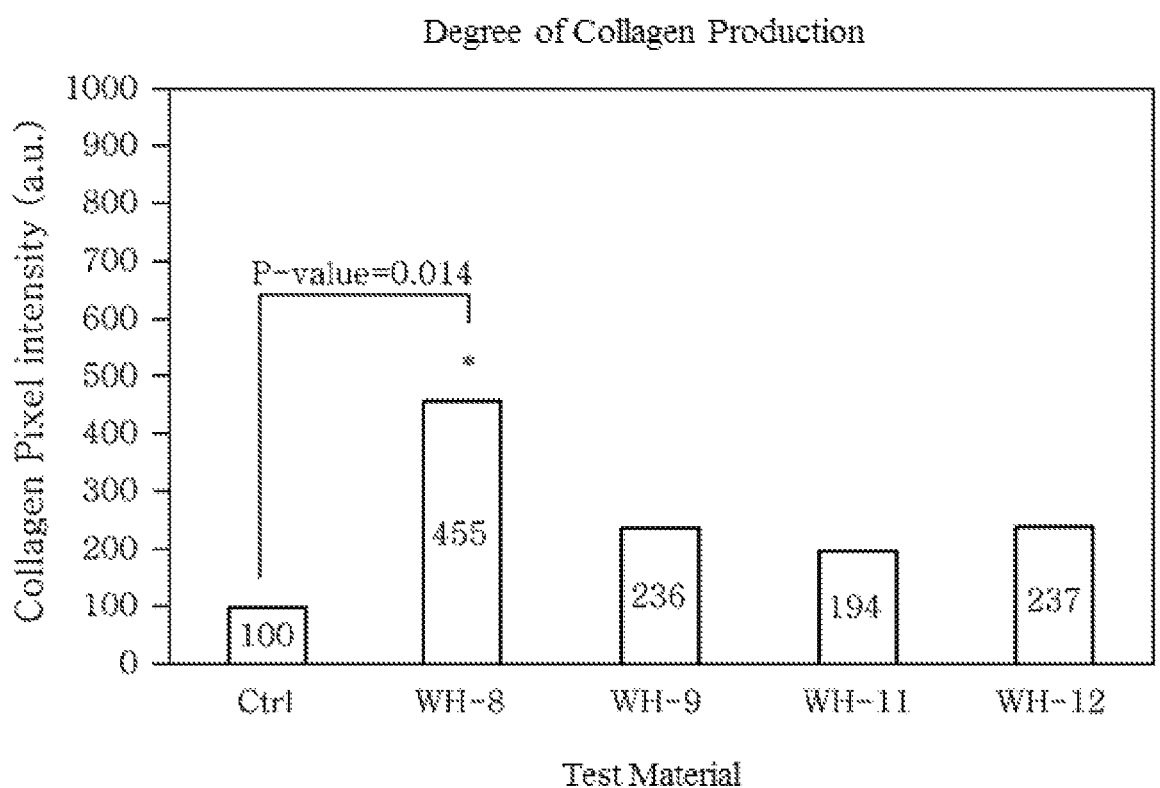

PEPTIDE AND COMPOSITION CONTAINING THE SAME FOR ANTI-INFLAMMATION, ANTI-FIBROSIS, WOUND HEALING, AND ANTICANCER TREATMENT

PRIORITY

This application is a National Stage Application based on International PCT Application PCT/KR2016/005529, filed on May 25, 2016, which claims priority to Korean Patent Application No. 10-2015-0073188 filed on May 26, 2015, the disclosures of which are herein incorporated by reference in their entireties.

REFERENCE TO SEQUENCE LISTING SUBMITTED ELECTRONICALLY

The instant application contains a sequence listing which has been submitted electronically in ASCII format and is hereby incorporated by reference in its entirety (said ASCII copy, created on Nov. 21, 2017, is named 2473_1000001_SeqListing_ST25.txt and is 3229 bytes in size).

TECHNICAL FIELD

The present invention relates to a novel peptide and a composition including the same, and more particularly, to a composition including a novel peptide and effective in anti-inflammation, anti-fibrosis, wound healing, and anti-cancer treatment.

BACKGROUND ART

Tumor necrosis factor (TNF), especially TNF-α, is known to be released from inflammatory cells and thus cause a variety of cytotoxic, immune and inflammatory responses. It is known that TNF-α is involved in the development or prolongation of many inflammatory diseases and autoimmune diseases, and, when released into blood to act systemically, TNF-α causes severe septicemia and septicemic shock. As such, since TNF-α is a factor widely involved in the immune system of a living body, drugs for inhibiting TNF-α have been actively developed. TNF-α is biosynthesized in an inactive form and cleaved by a protease to become an active form, and an enzyme involved in this activation is referred to as a tumor necrosis factor-converting enzyme (TACE). Thus, substances for inhibiting the TACE may treat, alleviate, and prevent diseases, conditions, abnormal conditions, poor conditions, poor subjective symptoms, and the like that are caused by TNF-α (KR2011-0060940A).

Fibrosis is a disease that causes abnormal formation, accumulation, and deposition of extracellular matrices by fibroblasts, and refers to abnormal accumulation of collagen matrixes due to injury or inflammation that changes the structure and function of various tissues. Regardless of the onset location of fibrosis, most etiology of fibrosis includes excessive accumulation of collagen matrices replacing normal tissues. In particular, fibrosis occurring in the kidneys, the liver, the lungs, the heart, bones or bone marrow, and skin induces dysfunction of organs and eventually leads to death in severe cases. The fibroblasts serve to form an extracellular matrix precursor under a normal condition to form a fibrous tissue. The extracellular matrix, which is an intercellular substance of connective tissues, exists in the form of proteins such as fibronectin, laminin, chondronectin, and collagen.

Meanwhile, TGF-β plays a very diverse role in abnormal formation and accumulation of extracellular matrices by fibroblasts, cell proliferation, inflammatory responses, and cancer cell metastasis, and many cellular signaling pathways and targets have been identified. Thus, research into TGF-β has been conducted in many disease models, and research into and drug development of fibrotic diseases and cancer have been most actively conducted. TGF-β, which is a cell proliferation regulatory factor, has been reported to induce or restrict cell proliferation and thus play a vital role in the development of various diseases including cancer, heart diseases, and diabetes, and various physiological activities thereof have been reported. For example, there are actions such as the inhibition of TGF-β synthesis (the inhibition of the production of cell proliferation regulatory factors), TGF-β antagonist action (the disturbance of TGF receptors and signal transduction hindrance), platelet-derived growth factor (PDGF) antagonist action (the inhibition of angiogenesis inducing factors), p38 MAP kinase inhibitor action (the inhibition of cell proliferation signaling enzymes), anti-inflammation (the inhibition of TNF-alpha and MAPK production), and the like. Thus, if a novel pharmaceutical composition capable of more directly inhibiting TGF-β or blocking signal transduction pathways involved by TGF-β, and having no side effects can be developed, a variety of diseases caused by fibrosis and aging may be prevented and treated.

The wound healing process is largely divided into inflammation, granulation, epithelialization, and fibroplasia. In inflammation, necessary cells (fibroblasts, epithelial cells, etc.) are activated. Subsequently, in granulation, fibroblasts deposit collagen, and thus the amount of collagens increases and a wound becomes mature. In addition, changes in keratinocytes occur at the wound site, and the epidermis of the wound site becomes thick and gradually proceeds into a state in which epithelial cells transfer from basal cells below the epidermis to the epidermis, which is referred to as epithelialization. As fibroplasia proceeds through the epithelialization, collagen fibers form a collagenous matrix to fill the wound site, and this process continues to proceed for a long period of time and is terminated, thereby completing wound healing. Thus, the proliferation of epithelial cells and the production of collagen may also be considered as an important mechanism in wound healing and antiaging action.

DISCLOSURE

Technical Problem

Under these circumstances, the inventors of the present invention developed novel peptides and discovered that the novel peptides were effective in inflammation, anti-fibrosis, wound healing, anticancer treatment, and the like by reducing TNF-α and inhibiting TGF-β, thus completing the present invention.

An object of the present invention is to provide novel peptides effective in anti-inflammation, anti-fibrosis, wound healing, and anticancer treatment, and compositions for preventing or treating a disease which include the novel peptides.

Technical Solution

An embodiment of the present invention provides a peptide having an amino acid sequence represented by one of SEQ ID NOS: 1 to 10 and 12, a peptide being a fragment of a sequence of the peptide, a peptide having 80% or more sequence homology to the sequence of the peptide or a fragment thereof, or a pharmaceutically acceptable salt thereof.

An embodiment of the present invention provides an anti-inflammatory composition including the peptide or a pharmaceutically acceptable salt thereof.

In one embodiment, the anti-inflammatory composition according to the present invention may have an anti-inflammatory activity by TNF-α inhibition.

In one embodiment, the anti-inflammatory composition according to the present invention prevents or treats any one or more inflammation-associated diseases selected from the group consisting of rheumatoid arthritis, psoriasis, psoriatic arthritis, atopic dermatitis, inflammatory bowel diseases such as ulcerative colitis, Crohn's disease, and the like, ankylosing spondylitis, multiple sclerosis, systemic lupus erythematosus (SLE), chronic obstructive pulmonary disease (COPD), septicemia, endotoxin shock, hepatitis, and type 1 diabetes.

An embodiment of the present invention provides a composition for preventing, treating, or alleviating fibrosis of a body organ, the composition including the peptide or a pharmaceutically acceptable salt thereof.

In one embodiment, the composition for preventing, treating, or alleviating fibrosis of a body organ, according to the present invention, has an activity of inhibiting fibrosis of a body organ by TGF-β signaling inhibition.

In one embodiment, the composition for preventing, treating, or alleviating fibrosis of a body organ, according to the present invention, prevents or treats fibrosis induced by one or more selected from the group consisting of cancer, administration of an anticancer drug, and radiation exposure.

In one embodiment, the composition for preventing, treating, or alleviating fibrosis of a body organ, according to the present invention, prevents or treats fibrosis of cell tissues of cancer selected from the group consisting of pancreatic cancer, colon cancer, stomach cancer, prostate cancer, non-small cell lung cancer, breast cancer, melanoma, and ovarian cancer.

An embodiment of the present invention also provides a composition for treating or alleviating a wound, the composition including the peptide or a pharmaceutically acceptable salt thereof.

In one embodiment, the composition for treating or alleviating a wound, according to the present invention, has a wound healing effect by inducing collagen synthesis.

In one embodiment, the composition for treating or alleviating a wound, according to the present invention, prevents or treats a skin disease selected from the group consisting of skin wrinkles, skin dryness, skin dents, epidermal burns, epidermal lacerations, epidermal wounds, and combinations thereof; or aggravation thereof.

In one embodiment of the present invention, the composition may be a composition for improving a skin condition which includes one or more of the peptides or a salt thereof. In one embodiment, the skin condition may be any one of skin wrinkles according to skin aging, skin dryness, reduced skin elasticity, and skin dents. In one embodiment, the composition may be a cosmetic composition.

In one embodiment of the present invention, the composition may be anti-cancer composition including one or more of the peptides or a salt thereof.

An embodiment of the present invention also provides a kit used for one or more effects selected from anti-inflammation, anti-fibrosis, anti-cancer treatment, wound healing, and skin condition improvement, the kit including: a composition including the peptide or a pharmaceutically acceptable salt thereof; and an instruction instructing one or more selected from a dose, administration route, the number of doses, and indications of the composition.

An embodiment of the present invention also provides a method of alleviating, preventing, or treating inflammation, fibrosis, cancer, or wound; or improving a skin condition, the method including administering a composition including the peptide or a pharmaceutically acceptable salt thereof to a subject in need of any one or more effects selected from anti-inflammation, anti-fibrosis, anti-cancer treatment, wound healing, and skin condition improvement.

An embodiment of the present invention provides a novel use of the peptide or a pharmaceutically acceptable salt thereof. In one embodiment, the use may be alleviation, prevention, or treatment of inflammation, fibrosis, cancer, or a wound. In another embodiment, the use may be skin condition improvement. In one embodiment, the skin condition may any one or more of skin wrinkles according to skin aging, skin dryness, reduced skin elasticity, and skin dents. For example, the use may be a use as a cosmetic composition.

An embodiment of the present invention provides a peptide for alleviating, preventing, or treating inflammation, fibrosis, cancer, or a wound, or a salt thereof.

Advantageous Effects

Peptides having sequences of SEQ ID NOS according to the present invention are effective in anti-inflammation, anti-fibrosis, wound healing, and anticancer treatment, and thus a method of preventing or treating diseases associated with inflammation, fibrosis, wound, and cancer is expected to be provided.

DESCRIPTION OF DRAWINGS

FIG. 1 is a graph showing RT-qPCR measurement results of mRNA expression amounts of TNF-α of an LPS-treated THP-1 cell line treated with each of the novel peptides of Pep-WH-1 to Pep-WH-12 at each concentration (1 μM, 5 μM, and 10 μM), wherein the measurement results are represented as inhibition ratios.

FIG. 2 is a graph showing ELISA measurement results of the amounts of TNF-α of experimental groups obtained by administering each of the novel peptides of Pep-WH-1 to Pep-WH-12 to a THP-1 cell line in which inflammation was induced by LPS, at each concentration (1 μM, 5 μM, and 10 μM), a control treated with none, and a positive control treated with estradiol (E2).

FIG. 3 illustrates an image (upper side) and a graph (lower side) showing measurement results of the expression of phosphor-Smad 2/3 as a fibrosis marker, Smad 2/3, and a reference gene GAPDH, obtained by western blotting and using an image analyzer, of a control in which a HepG2 cell line was untreated, a fibrosis control treated only with TGF-β, a positive control treated with each of TGF-β and SB43152, and experimental groups treated with novel peptides of Pep-WH-1 to Pep-WH-4 at each concentration (1 μM and 10 μM).

FIG. 4 illustrates an image (upper side) and a graph (lower side) showing measurement results of the expression of phosphor-Smad 2/3 as a fibrosis marker, Smad 2/3, and a reference gene GAPDH, obtained by western blotting and using an image analyzer, of a control in which a HepG2 cell line was untreated, a fibrosis control treated only with TGF-β, a positive control treated with each of TGF-β and SB43152, and experimental groups treated with novel peptides of Pep-WH-5 to Pep-WH-8 at each concentration (1 μM and 10 μM).

FIG. 5 illustrates an image (upper side) and a graph (lower side) showing measurement results of the expression of phosphor-Smad 2/3 as a fibrosis marker, Smad 2/3, and a reference gene GAPDH, obtained by western blotting and using an image analyzer, of a control in which a HepG2 cell line was untreated, a fibrosis control treated only with TGF-β, a positive control treated with each of TGF-β and SB43152, and experimental groups treated with novel peptides of Pep-WH-9 to Pep-WH-12 at each concentration (1 μM and 10 μM).

FIG. 6 is a graph showing measurement results of wound areas of a non-treated control and a wound-induced animal model obtained by inducing a wound in SD rats, obtained immediately after the wound (day 0) and on day 1, day 3, day 5, day 7, day 10, and day 11, wherein the wound-induced animal model was treated with 50 μL of the novel peptide Pep-WH-8 at a concentration of 100 μg/mL immediately after the wound and every two days.

FIG. 7 is a graph showing measurement results of wound areas of a non-treated control and a wound-induced animal model obtained by inducing a wound in SD rats, obtained immediately after the wound (day 0) and on day 1, day 3, day 5, day 7, day 10, and day 11, wherein the wound-induced animal model was treated with 50 μL of the novel peptide Pep-WH-9 at a concentration of 100 μg/mL immediately after the wound and every two days.

FIG. 8 is a graph showing measurement results of wound areas of a non-treated control and a wound-induced animal model obtained by inducing a wound in SD rats, obtained immediately after the wound (day 0) and on day 1, day 3, day 5, day 7, day 10, and day 11, wherein the wound-induced animal model was treated with 50 μL of the novel peptide Pep-WH-11 at a concentration of 100 μg/mL immediately after the wound and every two days.

FIG. 9 is a graph showing measurement results of wound areas of a non-treated control and a wound-induced animal model obtained by inducing a wound in SD rats, obtained immediately after the wound (day 0) and on day 1, day 3, day 5, day 7, day 10, and day 11, wherein the wound-induced animal model was treated with 50 μL of the novel peptide Pep-WH-12 at a concentration of 100 μg/mL immediately after the wound and every two days.

FIG. 10 is a graph showing average fluorescence intensity measurement results of the degree of collagen production of Masson trichrome-stained biopsy tissues of two rats on day 3 and day 5 taken from each of a non-treated control and experimental groups obtained by treating wound-induced SD rats as a wound-induced animal model with 50 μL of each of the novel peptides Pep-WH-8, Pep-WH-9, Pep-WH-11, and Pep-WH-12 at a concentration of 100 μg/mL, immediately after the wound and every two days.

BEST MODE

Although the present invention allows for various changes and numerous embodiments, particular embodiments of the present invention will now be described in more detail. However, it is not intended to limit the present invention to particular modes of practice, and it should be construed as including all changes, equivalents, and substitutes within the spirit and scope of the present invention. In the description of the present invention, certain detailed explanations of related art are omitted when it is deemed that they may unnecessarily obscure the essence of the invention.

According to an embodiment of the present invention, a novel peptide having a sequence of one of SEQ ID NOS: 1 to 10 and 12 is provided.

A peptide disclosed in the present specification may include peptides having 80% or more sequence homology, 85% or more sequence homology, 90% or more sequence homology, 95% or more sequence homology, 96% or more sequence homology, 97% or more sequence homology, 98% or more sequence homology, and 99% or more sequence homology to the novel peptide having a sequence of any one of SEQ ID NOS: 1 to 10 and 12. In addition, the peptide disclosed in the present specification may include the peptide having a sequence of any one of SEQ ID NOS: 1 to 10 and 12, and a peptide in which one or more amino acids, two or more amino acids, three or more amino acids, four or more amino acids, five or more amino acids, six or more amino acids, or seven or more amino acids are modified.

In one embodiment of the present invention, an amino acid modification refers to a change in physical and chemical properties of peptides. For example, amino acid modifications to improve thermal stability of peptides, change substrate specificity, change the optimum pH, and the like may be performed.

The term "amino acid" as used herein includes 22 standard amino acids naturally incorporated into peptides, in addition to D-isomers and modified amino acids thereof. Accordingly, the peptide according to an embodiment of the present invention may be a peptide including D-amino acids. Meanwhile, a peptide according to another embodiment of the present invention may include non-standard amino acids produced by post-translational modifications. Examples of the post-translational modification include phosphorylation, glycosylation, acylation (including, for example, acetylation, myristoylation, and palmitoylation), alkylation, carboxylation, hydroxylation, glycation, biotinylation, ubiquitinylation, modification of chemical properties (e.g., beta-elimination deimidation and deamidation), and structural modification (e.g., formation of disulfide bridges). In addition, the post-translational modification includes modification of amino acids resulting from chemical reactions occurring in binding with cross-linkers for forming a peptide conjugate, for example, modification of amino acids, such as a change in amino group, carboxyl group, or side chains.

The peptide disclosed in the present specification may be a wild-type peptide identified and isolated from naturally occurring sources. Meanwhile, the peptide disclosed in the present specification may be an artificial variant having an amino acid sequence in which one or more amino acids are substituted, deleted, and/or inserted, compared to peptides, which are fragments of SEQ ID NO: 1. Modifications of amino acids in wild-type polypeptides as well as the artificial variant include conservative amino acid substitution that does not significantly affect folding and/or activity of a protein. Examples of the conservative amino acid substitution include substitution of basic amino acids (arginine, lysine, and histidine), acidic amino acids (glutamic acid and aspartic acid), polar amino acids (glutamine and asparagine), hydrophobic amino acids (leucine, isoleucine, valine, and methionine), aromatic amino acids (phenylalanine, tryptophan, and tyrosine), and small amino acids (glycine, alanine, serine, and threonine). Generally, amino acid substitutions that do not change specific activity are known in the art. The most commonly occurring substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly, and substitutions thereof in the opposite direction. Other examples of conservative substitutions are shown in the following table.

TABLE 1

| Original amino acid | Exemplary residue substitution | Preferable residue substitution |
|---|---|---|
| Ala (A) | val; leu; ile | Val |
| Arg (R) | lys; gln; asn | Lys |
| Asn (N) | gln; his; asp, lys; arg | Gln |
| Asp (D) | glu; asn | Glu |
| Cys (C) | ser; ala | Ser |
| Gln (Q) | asn; glu | Asn |
| Glu (E) | asp; gln | Asp |
| Gly (G) | Ala | Ala |
| His (H) | asn; gln; lys; arg | Arg |
| Ile (I) | leu; val; met; ala; phe; norleucine | Leu |
| Leu (L) | norleucine; ile; val; met; ala; phe | Ile |
| Lys (K) | arg; gln; asn | Arg |
| Met (M) | leu; phe; ile | Leu |
| Phe (F) | leu; val; ile; ala; tyr | Tyr |
| Pro (P) | Ala | Ala |
| Ser (S) | thr | Thr |
| Thr (T) | Ser | Ser |
| Trp (W) | tyr; phe | Tyr |
| Tyr (Y) | trp; phe; thr; ser | Phe |
| Val (V) | ile; leu; met; phe; ala; norleucine | Leu |

The substantial modification of the biological properties of peptides may be performed by selecting substitution sites in which: (a) effects of the substantial modification in maintaining the structure of a polypeptide backbone in a substitution region, e.g., a sheet or helical three-dimensional structure, (b) effects thereof in maintaining charges or hydrophobicity of the molecule in a target site, or (c) effects thereof in maintaining the bulk of side chains are significantly different. Natural residues are divided into the following groups based on general side chain properties:
(1) Hydrophobicity: Norleucine, met, ala, val, leu, ile;
(2) Neutral hydrophilicity: cys, ser, thr;
(3) Acidity: asp, glu;
(4) Basicity: asn, gln, his, lys, arg;
(5) Residues that affect chain orientation: gly, pro; and
(6) Aromaticity: trp, tyr, phe.

Non-conservative substitutions may be performed by exchanging a member of any one of these classes for another class. Any cysteine residues that have no relation to maintaining the proper stereoscopic structure of peptides are generally substituted with serine, and thus may improve oxidative stability of the molecules and prevent improper crosslinking. Conversely, cysteine bond(s) may be added to the peptide to improve stability thereof.

Other types of amino acid variants of peptides are those in which antibody glycosylation patterns are changed. The term "change" as used herein refers to deletion of one or more carbohydrate residues found in peptides and/or addition of one or more glycosylation sites not present in peptides.

The glycosylation of peptides is typically N-connected or O-connected. The term "N-connected" as used herein indicates that a carbohydrate residue is attached to the side chain of an asparagine residue. As tripeptide sequences, asparagine-X-serine and asparagine-X-threonine, wherein X is any amino acid except for proline, are recognition sequences for enzymatically attaching a carbohydrate residue to the side chain of asparagine. Thus, as one of these tripeptide sequences is present in a polypeptide, a potential glycosylation site is generated. O-connected glycosylation means attaching any one of sugar N-acetylgalactosamine, galactose, and xylose to hydroxyl amino acid, most commonly, serine or threonine, but 5-hydroxyproline or 5-hydroxylysine may be used.

Addition of a glycosylation site to a peptide is conveniently performed by changing an amino acid sequence to contain the aforementioned one or more tripeptide sequence (in the case of N-connected glycosylation site). These changes may be made by addition of one or more serine or threonine residues to the sequence of an initial antibody or by substitution thereof with these residues (in the case of O-connected glycosylation site).

In addition, the peptide having a sequence of any one of SEQ ID NOS: 1 to 10 and 12 according to an embodiment of the present invention has low intracellular toxicity and is highly stable in vivo. Each of the peptides of SEQ ID NOS: 1 to 10 and 12 according to the present invention is a peptide having a length of 8 amino acids as follows.

The peptides of SEQ ID NOS: 1 to 10 and 12 are shown in Table 2 below. The term "name" shown in Table 2 is used to distinguish the peptides from one another.

TABLE 2

| SEQ ID NO. | Name | Sequence | Molecular weight |
|---|---|---|---|
| 1 | Pep-WH-1 | ALSSRLRA | 872.52 |
| 2 | Pep-WH-2 | ALSSRLRG | 858.50 |
| 3 | Pep-WH-3 | ALSSRLRF | 948.55 |
| 4 | Pep-WH-4 | ALSTRLRA | 886.53 |
| 5 | Pep-WH-5 | ALSTRLRG | 872.52 |
| 6 | Pep-WH-6 | ALSTRLRF | 962.57 |
| 7 | Pep-WH-7 | ALTSRVRA | 872.52 |
| 8 | Pep-WH-8 | ALTSRVRG | 858.50 |
| 9 | Pep-WH-9 | ALTSRVRF | 948.55 |
| 10 | Pep-WH-10 | ALTSKLRA | 858.53 |
| 12 | Pep-WH-12 | ALTSKLRF | 934.56 |

An embodiment of the present invention also provides a pharmaceutical composition including one or more selected from peptides having amino acid sequences of SEQ ID NOS: 1 to 10 and 12 as an active ingredient.

In a pharmaceutical composition for preventing or treating diseases associated with inflammation, fibrosis, wound, and cancer according to an embodiment of the present invention, the content of the peptide of any one of SEQ ID NOS: 1 to 10 and 12 may range from 0.01 mg/mL to 0.1 mg/mL, 1 mg/mL, 10 mg/mL, and 100 mg/mL. However, when a difference in effects according to dose is shown, the content thereof may be appropriately adjusted. When the content of each peptide is within the above range, not only it is sufficient to exhibit desired effects of the present invention, but also both stability and safety of the composition may be satisfied, and it may be appropriate in terms of effects relative to costs.

The composition according to an embodiment of the present invention may be applied to all animals including humans, dogs, chickens, pigs, cows, sheep, guinea pigs, or monkeys.

The pharmaceutical composition according to an embodiment of the present invention may be administered orally, intrarectally, percutaneously, intravenously, intramuscularly, intraperitoneally, intramedullary, intradurally, subcutaneously, or the like.

A preparation for oral administration may be a tablet, a pill, a soft or hard capsule, a granule, powder, a liquid preparation, or an emulsion, but the present invention is not limited thereto. A formulation for parenteral administration may be an injection, a dripping agent, a lotion, an ointment, a gel, a cream, a suspension, an emulsion, a suppository, a patch, or a spraying agent, but the present invention is not limited thereto.

The pharmaceutical composition according to an embodiment of the present invention may include an additive such as a diluent, an excipient, a lubricant, a binder, a disintegrant, a buffer, a dispersant, a surfactant, a colorant, a flavoring, a sweetener, or the like according to need. The pharmaceutical composition according to an embodiment of the present invention may be prepared using a method commonly used in the art.

The active ingredient of the pharmaceutical composition according to an embodiment of the present invention may vary depending on the age, gender, body weight, pathologic conditions and severity of subjects to which the active ingredient is to be administered, and administration route, or determination of prescribers. Determination of a suitable dose based on these factors may be within the range known by those of ordinary skill in the art, and a daily dose of the pharmaceutical composition may range, for example, from 0.1 µg/kg/day to 100 g/kg/day, in particular, from 10 µg/kg/day to 10 g/kg/day, more particularly, from 100 µg/kg/day to 1 g/kg/day, even more particularly, from 500 µg/kg/day to 100 mg/kg/day. When a difference in effects according to dose is shown, the daily dose may be appropriately adjusted. The pharmaceutical composition according to an embodiment of the present invention may be administered once to three times daily, but the present invention is not limited thereto.

A preparation of the composition according to an embodiment of the present invention is not particularly limited, and may be formulated as, for example, a tablet, a granule, powder, a liquid preparation, a solid preparation, or the like. Each preparation may be prepared by formulating ingredients commonly used in the art in addition to the active ingredient or appropriately selecting and mixing the ingredients by one of ordinary skill without undue difficulty according to the purpose of use. In addition, when used simultaneously with other raw materials, the ingredients may have a synergistic effect.

The composition including the peptide according to an embodiment of the present invention may be used as a pharmaceutical composition for preventing or treating one or more inflammation-associated diseases selected from the group consisting of rheumatoid arthritis, psoriasis, psoriatic arthritis, atopic dermatitis, inflammatory bowel diseases such as ulcerative colitis, Crohn's disease, and the like, ankylosing spondylitis, multiple sclerosis, systemic lupus erythematosus (SLE), chronic obstructive pulmonary disease (COPD), septicemia, endotoxin shock, hepatitis, and type 1 diabetes.

The composition including the peptide according to an embodiment of the present invention may be used as a pharmaceutical composition for preventing or treating fibrosis induced by one or more selected from the group consisting of cancer, administration of an anticancer drug, and radiation exposure.

The pharmaceutical composition for preventing or treating fibrosis which includes the peptide according to an embodiment of the present invention may exhibit an effect of inhibiting the fibrosis of cell tissues of cancer selected from the group consisting of pancreatic cancer, colon cancer, stomach cancer, prostate cancer, non-small cell lung cancer, breast cancer, melanoma, and ovarian cancer.

The composition including the peptide according to an embodiment of the present invention may be used as a pharmaceutical composition for preventing or treating and alleviating a skin disease selected from the group consisting of skin wrinkles, skin dryness, skin dents, epidermal burns, epidermal lacerations, epidermal wounds, and combinations thereof; or aggravation thereof.

An embodiment of the present invention provides a cosmetic composition including the peptide or a salt thereof. The cosmetic composition includes a cosmetically or dermatologically acceptable medium or base. The cosmetic composition may be in any form suitable for local application, for example, a solution, a gel, a solid, a paste anhydrous product, an emulsion obtained by dispersing an oil phase in water phase, an emulsion obtained by dispersing a water phase in an oil phase, a multi-emulsion, a suspension, a microemulsion, a microcapsule, microgranules, ionic (liposome) and non-ionic vesicle dispersants, a foam, and an aerosol or patch form further containing a compressed propellant. These preparations may be prepared according to a method commonly used in the art.

The cosmetic composition preferably includes other ingredients capable of imparting a synergistic effect to the main effect within a range that does not adversely affect the main effect, in addition to the above-described materials, and may be mixed with other ingredients in addition to the active ingredient, appropriately selected by one of ordinary skill in the art without any undue difficulty according to preparations of other cosmetic compositions or the purpose of use thereof. For example, the cosmetic composition of the present invention may include, in addition to the active ingredient, other ingredients mixed in a general cosmetic composition according to need, and examples thereof include oil and fat ingredients, a moisturizing agent, an emollient agent, a surfactant, organic and inorganic pigments, organic powders, an ultraviolet absorbent, a preservative, a bactericide, an antioxidant, a stabilizer, a thickener, glycerin, a pH adjuster, alcohols, dyes, a pigment, flavoring, a blood circulation promoter, a cooling agent, an antiperspirant, purified water, and the like. Other mixed ingredients that may be included in the cosmetic composition are not limited to the above examples, and mixing amounts of the ingredients may be within a range that does not adversely affect the objectives and effects of the present invention.

Preparations of the cosmetic composition are not particularly limited, and may be appropriately selected to the purpose of use. For example, the cosmetic composition may be in the form of one or more preparations selected from the group consisting of soap-type preparations, skin toner, nutrition lotion, essence, nutrition cream, massage cream, pack, gel, makeup base, foundation, powder, lipsticks, patches, aerosol, eye cream, eye essence, cleansing cream, cleansing foam, cleansing water, a cleanser, hair shampoo, hair conditioning, hair treatment, hair essence, hair lotion, scalp hair tonic, scalp essence, hair gel, hair spray, hair pack, body lotion, body cream, body oil, and body essence, but the present invention is not limited to the above examples.

Preparations of a food composition according to the present specification are not particularly limited, but the food composition may be formulated into, for example, tablets, granules, powders, a liquid such as a drink, caramel, gel, a bar, or the like. The food composition of each preparation may include mixed ingredients commonly used in the art in addition to the active ingredient, appropriately selected by one of ordinary skill in the art without any difficulty according to preparations or the purpose of use, and, when these ingredients as well as other raw materials are simultaneously applied, synergistic effects may be obtained.

In the food composition according to the present specification, dose of the active ingredient may be determined by those of ordinary skill in the art, and a daily dose of the food composition may be not limited to, for example, 0.1 mg/kg/day to 5,000 mg/kg/day, more particularly, 50 mg/kg/day to 500 mg/kg/day, and may vary depending on various factors such as ages of subjects to be administered, health conditions, complications, and the like.

The food composition according to the present specification may be, for example, a variety of foods such as chewing gums, caramel products, candies, ice creams, confectionery, and the like, beverage products such as alcohol drinks, and the like, or health functional foods including vitamins, minerals, or the like.

In addition, the food composition according to an embodiment of the present invention may include various nutritional supplements, vitamins, minerals (electrolytes), flavors such as synthetic flavors, natural flavors, and the like, colorants and enhancers (cheese, chocolates, and the like), pectic acid and salts thereof, alginic acid and salts thereof, organic acids, a protective colloid thickener, a pH adjuster, a stabilizer, a preservative, glycerin, alcohols, a carbonating agent used in carbonated beverages, and the like. In addition, the functional food compositions of the present invention may include flesh for the preparation of natural fruit juice, fruit juice beverages, and vegetable beverages. These ingredients may be used alone or a combination thereof may be used. The proportion of these additives is not much important, but the amounts of the additives generally range from 0 part by weight to about 20 parts by weight with respect to 100 parts by weight of the composition of the present invention.

Terms used in the present specification are provided only to describe particular embodiments, and are not intended to limit the present invention. Terms that do not mention whether the noun is singular or plural are not intended to limit the number, but indicate that the mentioned noun exists in either a singular or plural form. The terms "including," "having," and "comprising" are interpreted as open terms (i.e., including, but not limited thereto).

Referring to a range of the values is an easy way to avoid individually mentioning each separate value within the range, and, unless otherwise stated herein, each separate value is incorporated in the present specification as if it is individually mentioned herein. The limit values of all the ranges are within the ranges and may be independently combined.

All the methods mentioned herein may be performed in a suitable order unless otherwise indicated or clearly contradicted by the context. The use of any one embodiment and all embodiments or exemplary languages (e.g., "such as") is intended to more fully describe the present invention and is not intended to limit the scope of the present invention unless it is within the claims. Any language in the specification should not be interpreted such that any unclaimed elements are essential to the practice of the present invention. Unless otherwise defined, technical and scientific terms used herein have the same meaning as commonly understood by one of ordinary skill in the art to which the invention pertains.

Exemplary embodiments of the present invention include the best mode known to inventors to implement the present invention. Variations of the exemplary embodiments may be obvious to those of ordinary skill in the art after reading the foregoing description. The inventors of the present invention expect that one of ordinary skill in the art appropriately uses such variations, and expect that the present invention is carried out in a manner different from that described herein. Thus, the present invention includes equivalents to and all modifications of the subject matter of the invention mentioned in the appended claims, as is permitted by the patent laws. In addition, all possible combinations of the aforementioned elements are included in the present invention within all possible variations when stated in a contrary manner or unless clearly contradicted by the context. Although the present invention has been described in detail with reference to exemplary embodiments thereof, it will be well understood by those of ordinary skill in the art that various changes in form and details can be made without departing from the spirit and scope of the invention defined by the following claims.

MODE

Hereinafter, constitutions and effects of the present invention will be described in further detail with reference to Examples and Experimental Examples. However, these Examples and Experimental Examples are provided for illustrative purposes only to aid in understanding the present invention and are not intended to limit the spirit and the scope of the present invention.

Example 1: Synthesis of Novel Peptides

Novel peptides of SEQ ID NOS: 1 to 10 and 12 (hereinafter, referred to as "Pep-WH-1 to Pep-WH-12") were prepared according to a generally known solid-phase peptide synthesis method. In particular, peptides were synthesized by Fmoc solid phase peptide synthesis (SPPS) using ASP48S (Peptron, Inc., Daejeon, Korea) by coupling amino acids one by one from the C-terminal. A complex in which the first amino acid at the C-terminus of each of the peptides was attached to a resin was used. For example:

$NH_2$-Lys(Boc)-2-chloro-Trityl Resin
$NH_2$-Ala-2-chloro-Trityl Resin
$NH_2$-Arg(Pbf)-2-chloro-Trityl Resin All amino acids used in the peptide synthesis were protected by Trt, Boc, t-butylester (t-Bu), 2,2,4,6,7-pentamethyl dihydro-benzofuran-5-sulfonyl (Pbf), or the like, whereas the N-terminus was protected by Fmoc, and the residues were all removed in acid. For example, the amino acids were as follows:

Fmoc-Ala-OH, Fmoc-Arg(Pbf)-OH, Fmoc-Glu(OtBu)-OH, Fmoc-Pro-OH, Fmoc-Leu-OH, Fmoc-Ile-OH, Fmoc-Phe-OH, Fmoc-Ser(tBu)-OH, Fmoc-Thr(tBu)-OH, Fmoc-Lys(Boc)-OH, Fmoc-Gln(Trt)-OH, Fmoc-Trp(Boc)-OH, Fmoc-Met-OH, Fmoc-Asn(Trt)-OH, Fmoc-Tyr(tBu)-OH, Fmoc-Ahx-OH, Fmoc-Gln-OH, and Trt-Mercaptoacetic acid.

2-(1H-benzotriazole-1-yl)-1,1,3,3-tetamethylaminium hexafluorophosphate (HBTU)/N-hydroxybenzotriazole (HOBt)]/4-methylmorpholine (NMM) was used as a coupling reagent. Fmoc was removed using 20% piperidine in DMF. Each synthesized peptide was detached from the resin and the protective groups of the residues were removed using a cleavage cocktail [trifluoroacetic acid (TFA)/triisopropylsilane (TIS)/ethanedithiol (EDT)/$H_2O$=92.5/2.5/2.5/2.5].

Each peptide was synthesized by repeating a process of reacting a corresponding amino acid with a solid support to which a starting amino acid with a protective group bound thereto was bound, followed by washing with a solvent, and then deprotecting. The synthesized peptide was detached from the resin and purified with high performance liquid chromatography (HPLC), and then it was identified by LC/MS whether the peptide was synthesized or not, followed by lyophilization.

As a result of performing HPLC on the peptide used in the present embodiment, the purity of all the peptides was 95% or more.

A process of preparing the peptide Pep-WH-1 will now be described in detail as follows.

1) Coupling 8 equivalents of the protected amino acid and HBTU (8 equivalents)/HOBt (8 equivalents)/NMM (16 equivalents) as a coupling reagent were dissolved in DMF and added to $NH_2$-A-2-chloro-Trityl Resin, and then a reaction was allowed to occur therebetween at room temperature for 2 hours, and the reaction product was washed with DMF, MeOH, and DMF in this order.

2) Fmoc deprotection

20% piperidine in DMF was added to the resulting product, a reaction was allowed to occur therebetween at room temperature twice for 5 minutes, followed by washing with DMF, MeOH, and DMF in this order.

3) Reactions of 1) and 2) were repeated to thereby prepare $NH_2$-A-L-S(tBu)-S(tBu)-R(Pbf)-L-R(Pbf)-A-2-chloro-Trityl Resin as a peptide backbone.

4) Cleavage: The synthesis-completed peptide resin was treated with a cleavage cocktail to separate the peptide from the resin.

5) Cooling diethyl ether was added to the obtained mixture, and then the resulting mixture was centrifuged to precipitate the obtained peptide.

6) The crude peptide obtained in the above process was separated and purified using Prep HPLC. Vydac Everest C18 column (250 mm×22 mm, 10 µm) was used as a column. As an eluent, a water-acetonitrile linear gradient (10% to 75% (v/v) of acetonitrile) containing 0.1% (v/v) trifluoroacetic acid was used.

7) It was confirmed by LC/MS (Agilent HP1100 series) as to whether the separated peptide was synthesized to have the desired sequence.

8) It was confirmed by analytical HPLC as to whether the peptide, whose molecular weight had been identified, was separated and purified to 95% purity or higher, followed by lyophilization, to prepare Pep-WH-1 as white powder.

11 peptides of Pep-WH-2 to Pep-WH-12 were prepared using the same method as that used to prepare the peptide Pep-WH-1, except that the backbone of Pep-WH-1 was replaced by the corresponding sequence of each peptide.

Example 2: Anti-Inflammatory Activity of Novel Peptides

To verify the anti-inflammatory activity of each of the novel peptides Pep-WH-1 to Pep-WH-12, an expression degree of TNF-α known as a cytokine, which shows inflammatory activity in a cell line, in which inflammation had been induced with lipopolysaccharide (LPS), was measured for each peptide using RT-qPCR and ELISA.

Preparation of Experimental Reagents and Materials

An experiment was carried out using THP-1 cells (American Type Culture Collection (ATCC), Manassas, Va., USA), which is a human acute monocytic leukemia cell line. THP-1 cells were suspended in RPMI 1640 medium to a concentration of $1\times10^5$ cells per well in a 96 well plate and incubated for 24 hours. At this time, the THP-1 cells were treated with phorbol 12-myristate 13-acetate (PMA) (Sigma) to differentiate into macrophages.

Lipopolysaccharide (LPS, Sigma) was dissolved in phosphate buffered saline (PBS), and PMA was dissolved in dimethyl sulfoxide (DMSO).

The peptides Pep-WH-1 to Pep-WH-12 were synthesized in Peptron (Daejeon, Korea) according to the synthesis method used in Example 1 and used.

Experimental Method

The RT-qPCR test method was as follows. THP-1 cells were plated on a 6-well plate at a concentration of $2\times10^6$ cells/well and treated with 100 ng/mL of PMA for 24 hours to differentiate into macrophages. The media were removed and the differentiated THP-1 cells were washed twice with serum-free media (SFM), and then each novel peptide was treated with 10 ng/mL of LPS at each concentration of 1 µM, 5 µM, and 10 µM for 6 hours. RNA was extracted using RNeasy® Plus Mini Kit (Qiagen), and the extracted RNA was quantified and then cDNA synthesis was performed using a Reverse Transcription System (Promega). RT-qPCR was performed using a CFX96-Real-Time System (Bio-rad) to analyze mRNA expression of TNF-α, and GAPDH was used as a reference gene. 40 cycles of PCR were performed under the following conditions: at 95° C. for 15 seconds, at 55° C. for 30 seconds, and at 72° C. for 30 seconds), and used primer sequences are shown in Table 3 below.

TABLE 3

| Gene | Forward sequence (5'-3') | Reverse sequence (5'-3') |
|---|---|---|
| TNF-α | CTATCTGGGAGGGGTCTTCC (SEQ ID NO: 13) | ATGTTCGTCCTGCTCACAG (SEQ ID NO: 14) |
| GAPDH | AGGGCTGCTTTTAACTCTGGT (SEQ ID NO: 15) | CCCCACTTGATTTTGGAGG GA (SEQ ID NO: 16) |

The ELISA test method was as follows. THP-1, which is a monocyte cell line distributed from ATCC, was subcultured and prepared in the P3 stage, and the cell line was distributed into wells of a well plate and treated with PMA to differentiate into macrophages. The differentiated cells were treated with LPS to induce an inflammatory reaction (to induce the production of TNF-alpha), and were treated with each of the novel peptides at each concentration (1 µM, 5 µM, and 10 µM), and the amounts of TNF-α were measured by ELISA. Relative values for a non-inflammation group and a complete inflammation group were calculated, and estrogen (E2) was set as a positive control and a non-treated cell line not treated with the novel peptides was set as a general control to perform comparative analysis. E2 is known as a steroid that inhibits the production of TNF-α in THP-1.

Statistical Processing

All data are expressed as mean±standard error of the mean (S.E.M.), and statistical processing was performed by an ANOVA test. A SigmaStat statistical program was used and statistical analysis was performed using a Kruskal-Wallis test and a Mann-Whitney U-test. In addition, comparison between the groups was performed using a Tukey test and a p value less than 0.05 was determined as statistically significant.

Experimental Results and Analysis

Results measured by the experimental method are as follows.

As a result of comparing, through RT-qPCR, mRNA inhibition rates of TNF-α, indicating anti-inflammatory activity of each peptide through an expression amount of mRNA of TNF-α when THP-1 cells in which an inflammatory reaction had been induced with LPS were treated with each of the novel peptides at each concentration (1 μM, 5 μM, and 10 μM), all the peptides exhibited a concentration-dependent anti-inflammatory activity of 50% or more at 10 μM, and Pep-WH-11 exhibited the highest anti-inflammatory activity at 1 μM, which is the lowest treatment concentration (see FIG. 1).

As a result of confirming a capability of the THP-1 cells to inhibit the production of TNF-α through ELISA to evaluate the anti-inflammatory activities of the novel peptides, a low expression degree of TNF-α, i.e., inflammation-inducing activity, was exhibited in all the cases treated with the novel peptides at a concentration of 0.5 μM, compared to a none-treated control which was not treated with the novel peptides (See FIG. 2). When compared to E2 used as a positive control, among the novel peptides, Pep-WH-8, Pep-WH-9, Pep-WH-11, and Pep-WH-12 exhibited lower inflammation-inducing activity at all the concentrations.

Through the results of the two experiments, it can be confirmed that the novel peptides according to the present invention exhibit anti-inflammatory activity, confirmed by the inhibition of TNF-α. The experiment for the inhibition of TNF-α is known as the most basic experiment for verifying overall inflammation inhibitory effects, through which it is confirmed that the novel peptides of the present invention can have overall anti-inflammatory effects.

Example 3: Anti-Fibrotic Activity of Novel Peptides

To identify an inhibitory effect of TGF-β, considered as the main cause of fibrosis, of the novel peptides Pep-WH-1 to Pep-WH-12, an experiment for confirming a TGF-β signaling inhibitory action in a HepG2 cell line was carried out as follows.

Preparation of Experimental Reagents and Materials

Reagents and materials used in the present experiment are as follows. Powder-type novel peptides were dissolved in 0.2 μm filtered sterile water, and then stored in the form of aliquots at −70° C., and, when in use, the stored peptides were thawed. A HepG2 cell line (ATCC HB-8065; American Type Culture Collection) was used, and recombinant human TGF-β was dissolved in 4 mM HCl to prepare a 10 μg/mL stock. SB431542 (Sigma) as a positive control was used after being prepared into 10 mM stock.

Preparation of Cell Line $2 \times 10^6$ HepG2 cells (ATCC HB-8065) were seeded in a 60 mm petri dish, and then cultured in a $CO_2$ incubator for 16 hours. Subsequently, the medium was replaced by a serum-free medium (SFM) and further cultured for 24 hours. Thereafter, the medium was replaced with 10 ng/mL of TGF-β1, and the HepG2 cells were treated with each of the novel peptides at each concentration (1 μM and 10 μM) and then cultured for 72 hours. Groups treated with the respective novel peptides were further cultured in a $CO_2$ incubator at 37° C. for 1 hour.

Experimental Method

To measure anti-fibrotic activities of the novel peptides, an experiment for measuring a degree of TGF-β signaling inhibition was carried out by western blotting, and a detailed description of the experimental method is as follows.

Cells treated with each peptide were washed twice with PBS, collected in a 1.5 mL EP tube using a cell scraper, and then centrifuged using a centrifugal separator (1,000 rpm, 4° C., 2 minutes) to remove the supernatant, and then 100 μL each was added to RIPA-treated HepG2 cells. The HepG2 cells were incubated on ice for 40 minutes, and then mixed by shaking every 10 minutes (vertex, micro-centrifuge pre-cooled to 4° C.), and each sample was mixed 40 times to 50 times using a 1 mL syringe. Lastly, the resulting mixture was centrifuged at 13,000 rpm for 15 minutes and the obtained supernatant was used.

30 μg of protein was subjected to 8% sodium dodecyl sulfate-polyacrylamide gel electrophoresis (SDS-PAGE) to be transferred to polyvinylidene difluoride (PVDF) membranes (Millipore). The PVDF membranes were blocked with 5% skim milk and incubated with particular primary antibodies. The antibodies used in this experiment are as follows: Smad 2/3 (60, 52 kDa, 5% BSA 1:1000, #3102, Cell signaling), pSmad2/3 (cell signaling #3102), and GAPDH (37 kDa, 5% BSA 1:1000, #2118, Cell signaling). Subsequently, the PVDF membranes were washed with tris-buffered saline containing 0.1% Tween-20 (TBST), and then reacted with an HRP-conjugated anti-rabbit antibody (manufactured by Jackson ImmunoResearch Laboratories, Inc.). Afterwards, ECL detection (Amersham Pharmacia Biotech) was performed thereon, and the acquired images were analyzed using an image analyzer (GE Healthcare, ImageQuant LAS 4000).

To measure TGF-β inhibitory effects, pSmad2/3 and Smad2/3 were used as TGF-β signaling activity markers, and GAPDH was used as a reference group in electrophoresis. The TGF-β signaling activity markers which were expressed at a high concentration as TGF-β was inhibited were used.

Statistical Processing

All data are expressed as mean±S.E.M., and statistical processing was performed by an ANOVA test. The SigmaStat statistical program was used and statistical analysis was performed using a Kruskal-Wallis test and a Mann-Whitney U-test. In addition, comparison between the groups was performed using a Tukey test and a p value less than 0.05 was determined as statistically significant.

Experimental Results and Analysis

Results measured by the experimental method are as follows.

As a result of measuring degrees of TGF-β inhibition of the novel peptides through western blotting, high expression degrees of the markers, exhibited as the inhibition of TGF-β increased, were exhibited in all the cases treated with the novel peptides at a concentration of 10 μM, compared to an untreated fibrosis-induced group treated only with TGF-β (see FIGS. 3 to 5). From the results, it can be confirmed that TGF-β was inhibited by treatment with the novel peptides. In addition, compared to the case of the positive control treated with 10 μM SB431542, the groups treated with Pep-WH-3, Pep-WH-4, Pep-WH-5, Pep-WH-6, Pep-WH-7, and Pep-WH-12 at 10 μM each exhibited higher TGF-β inhibitory activity.

From the experimental results, it can be confirmed that the novel peptides according to the present invention exhibit anti-fibrotic activity shown by the inhibition of TGF-β. The experiment for the inhibition of TGF-β is known as a widely used anti-fibrotic activity experiment, through which it is confirmed that the novel peptides of the present invention can have anti-fibrotic activity effects.

Example 4: Wound Healing Activity of Novel Peptides

To confirm wound healing effects of the novel peptides Pep-WH-8, Pep-WH-9, Pep-WH-11, and Pep-WH-1, a wound-induced animal model was treated with each of the novel peptides, and then an experiment to confirm an effect of each peptide in producing collagen needed for a decrease in wound size and in a wound healing process was carried out as follows.

Preparation of Experimental Animal

Sprague-Dawley (SD) rats were selected because mice have thin skins and it is difficult to uniformly induce a wound in mice. To exclude effects due to hormonal changes, male SD rats were selected and 6-week-old SD rats were purchased and acclimated for about 1 week. However, to more precisely obtain experimental results, an experiment was carried out after the 6-week-old SD rats became 11 weeks old. Since experimental animals are sensitive to olfactory responses and may attack other individual, individuals were separated from each other after wounds were formed, such as 1 rat for each cage, and observed.

Experimental Method

The following method was used to form full-thickness excision in the prepared experimental animals. To induce anesthesia, a mixture of 10 mg/kg (body weight) of xylazine-HCl and 100 mg/kg (body weight) of ketamine HCl were intraperitoneally injected into the experimental animals or the experimental animals were administered the mixture via a respiratory anesthesia system. After the induction of anesthesia, hairs on the back of the experimental animal in a prone position were shaved cleanly, the back was disinfected with betadine, and then one circular full-thickness excision was made on a site apart from the highest portion of the back to each of left and right sides by a distance of about 1 cm, using a 16 mm punch. Separate dressing was not performed on the wound sites.

The full-thickness excision-induced animal model was divided into the following groups and a drug was applied on each group immediately after the formation of the excision and every two days. For the application method, a material was adjusted to a concentration of 1 mg/mL, and then, immediately before the experiment, the material was diluted 10 times to a concentration of 100 μg/mL. 50 μL of the material was applied dropwise on each excision.

1) Control: applying dropwise 50 μL of saline solution per one excision

2) Experimental group 1: applying dropwise 0.1 mg/mL of Pep-WH-8 in an amount of 50 μL per one excision 3) Experimental group 2: applying dropwise 0.1 mg/mL of Pep-WH-9 in an amount of 50 μL per one excision 4) Experimental group 3: applying dropwise 0.1 mg/mL of Pep-WH-11 in an amount of 50 μL per one excision 5) Experimental group 4: applying dropwise 0.1 mg/mL of Pep-WH-12 in an amount of 50 μL per one excision The groups were observed immediately after the formation of the excision and on day 2, day 4, day 7, day 9, day 11, and day 14 thereafter and photographed. When the wounds were completely healed, the wound healing date was recorded. Generally, on about day 9, individuals with the wound sizes decreased to 5% of the initial wounds began to appear. The wound sites were photographed with a ruler, and then the acquired images were analyzed using the Image J program (NIH, USA) to calculate wound areas, and the wound areas were compared with each other.

A biopsy for collagen formation was carried out by extracting wound sites of opposite sides of the back of each of two individuals of the control and two individuals of each experimental group on day 3 and day 5 after the formation of the excision. To compare as to whether collagen was synthesized, each group was subjected to Masson trichrome staining, and then average fluorescence intensity measurement values were obtained.

Experimental Results and Analysis

When comparing each experimental group with the control, the cases of Pep-WH-8 and Pep-WH-12 exhibited a smaller wound size on day 3 after inducing the full-thickness excision than that of the control (see FIGS. 6 and 9). The cases of Pep-WH-9 and Pep-WH-11 exhibited a smaller wound size on day 1 after inducing the full-thickness excision than that of the control (see FIGS. 7 and 8). When observing the control and the experimental groups on day 11, there was no significant difference between the wound sizes and the wounds became healed, but a smaller wound size in each experimental group than in the control at the early stage after the formation of the excision may indicate that the novel peptides are effective at an early stage of the excision formation.

In addition, in observation results of collagen formation after inducing the excision, all the experimental groups exhibited high average fluorescence intensity for collagen production, compared to the control (see FIG. 10). This may indicate that the novel peptides accelerate necessary collagen formation when wound sites are healed.

From the experimental results, it can be confirmed that the novel peptides according to the present invention have an activity of decreasing a wound formation area and increasing collagen synthesis. From this result, it is confirmed that the novel peptides of the present invention can have a wound healing activity effect.

Combining the results of Experimental Examples all together, the novel peptides according to the present invention may have anti-inflammatory, anti-fibrotic and wound healing effects, and may be used to develop a therapeutic agent for preventing or treating inflammation, fibrosis, and wound and also develop a medicine for preventing or treating cancer and various diseases with inflammation and fibrosis and a medicine for alleviating symptoms thereof.

The invention claimed is:

1. A peptide having an amino acid sequence of SEQ ID NO:12 or consisting of an amino acid sequence of SEQ ID NO:10.

2. A pharmaceutical composition comprising the peptide or a pharmaceutically acceptable salt thereof according to claim 1.

3. The pharmaceutical composition of claim 2, wherein the composition has an anti-inflammatory activity due to a decrease in TNF-α.

4. The pharmaceutical composition of claim 3, wherein the composition prevents or treats any one or more inflammation-associated diseases selected from the group consisting of rheumatoid arthritis, psoriasis, psoriatic arthritis, atopic dermatitis, inflammatory bowel diseases, ulcerative colitis, Crohn's disease, ankylosing spondylitis, multiple sclerosis, systemic lupus erythematosus (SLE), chronic obstructive pulmonary disease (COPD), septicemia, endotoxin shock, hepatitis, and type 1 diabetes.

5. The pharmaceutical composition of claim 2, wherein the composition alleviates fibrosis of a body organ.

6. The pharmaceutical composition of claim 5, wherein the composition has an activity of inhibiting fibrosis of a body organ by TGF-β signaling inhibition.

7. The pharmaceutical composition of claim 5, wherein the composition prevents or treats fibrosis induced by one or more selected from the group consisting of cancer, administration of an anticancer drug, and radiation exposure.

8. The pharmaceutical composition of claim 7, wherein the cancer is selected from the group consisting of pancreatic cancer, colon cancer, stomach cancer, prostate cancer, non-small cell lung cancer, breast cancer, melanoma, and ovarian cancer.

9. The pharmaceutical composition of claim 2, wherein the composition treats or alleviates a wound.

10. The pharmaceutical composition of claim 9, wherein the composition has a wound healing effect by inducing collagen synthesis.

11. The pharmaceutical composition of claim 9, wherein the wound is selected from the group consisting of epidermal burns, epidermal lacerations, epidermal wounds, and combinations thereof.

12. The pharmaceutical composition of claim 2, wherein the composition improves a skin condition.

13. The pharmaceutical composition of claim 12, wherein the skin condition is selected from the group consisting of skin wrinkles according to skin aging, skin dryness, scars, reduced skin elasticity, and skin dents.

14. The pharmaceutical composition of claim 2, wherein the composition is an anti-cancer composition.

15. A pharmaceutical kit comprising:
  the pharmaceutical composition according to claim 2; and
  an instruction instructing one or more selected from a dose, administration route, the number of doses, and indications of the composition.

16. A cosmetic composition comprising the peptide or a salt thereof according to claim 1.

* * * * *

SEQUENCE LISTING

<160> NUMBER OF SEQ ID NOS: 16

<210> SEQ ID NO 1
<211> LENGTH: 8
<212> TYPE: PRT
<213> ORGANISM: Artificial Sequence
<220> FEATURE:
<223> OTHER INFORMATION: Pep-WH-1 peptide

<400> SEQUENCE: 1

Ala Leu Ser Ser Arg Leu Arg Ala
1               5

```
<210> SEQ ID NO 2
<211> LENGTH: 8
<212> TYPE: PRT
<213> ORGANISM: Artificial Sequence
<220> FEATURE:
<223> OTHER INFORMATION: Pep-WH-2 peptide

<400> SEQUENCE: 2

Ala Leu Ser Ser Arg Leu Arg Gly
1               5

<210> SEQ ID NO 3
<211> LENGTH: 8
<212> TYPE: PRT
<213> ORGANISM: Artificial Sequence
<220> FEATURE:
<223> OTHER INFORMATION: Pep-WH-3 peptide

<400> SEQUENCE: 3

Ala Leu Ser Ser Arg Leu Arg Phe
1               5

<210> SEQ ID NO 4
<211> LENGTH: 8
<212> TYPE: PRT
<213> ORGANISM: Artificial Sequence
<220> FEATURE:
<223> OTHER INFORMATION: Pep-WH-4 peptide

<400> SEQUENCE: 4

Ala Leu Ser Thr Arg Leu Arg Ala
1               5

<210> SEQ ID NO 5
<211> LENGTH: 8
<212> TYPE: PRT
<213> ORGANISM: Artificial Sequence
<220> FEATURE:
<223> OTHER INFORMATION: Pep-WH-5 peptide

<400> SEQUENCE: 5

Ala Leu Ser Thr Arg Leu Arg Gly
1               5

<210> SEQ ID NO 6
<211> LENGTH: 8
<212> TYPE: PRT
<213> ORGANISM: Artificial Sequence
<220> FEATURE:
<223> OTHER INFORMATION: Pep-WH-6 peptide

<400> SEQUENCE: 6

Ala Leu Ser Thr Arg Leu Arg Phe
1               5

<210> SEQ ID NO 7
<211> LENGTH: 8
<212> TYPE: PRT
<213> ORGANISM: Artificial Sequence
<220> FEATURE:
<223> OTHER INFORMATION: Pep-WH-7 peptide

<400> SEQUENCE: 7

Ala Leu Thr Ser Arg Val Arg Ala
1               5
```

```
<210> SEQ ID NO 8
<211> LENGTH: 8
<212> TYPE: PRT
<213> ORGANISM: Artificial Sequence
<220> FEATURE:
<223> OTHER INFORMATION: Pep-WH-8 peptide

<400> SEQUENCE: 8

Ala Leu Thr Ser Arg Val Arg Gly
1               5

<210> SEQ ID NO 9
<211> LENGTH: 8
<212> TYPE: PRT
<213> ORGANISM: Artificial Sequence
<220> FEATURE:
<223> OTHER INFORMATION: Pep-WH-9 peptide

<400> SEQUENCE: 9

Ala Leu Thr Ser Arg Val Arg Phe
1               5

<210> SEQ ID NO 10
<211> LENGTH: 8
<212> TYPE: PRT
<213> ORGANISM: Artificial Sequence
<220> FEATURE:
<223> OTHER INFORMATION: Pep-WH-10 peptide

<400> SEQUENCE: 10

Ala Leu Thr Ser Lys Leu Arg Ala
1               5

<210> SEQ ID NO 11
<211> LENGTH: 8
<212> TYPE: PRT
<213> ORGANISM: Artificial Sequence
<220> FEATURE:
<223> OTHER INFORMATION: Pep-WH-11 peptide

<400> SEQUENCE: 11

Ala Leu Ser Thr Arg Leu Arg Gly
1               5

<210> SEQ ID NO 12
<211> LENGTH: 8
<212> TYPE: PRT
<213> ORGANISM: Artificial Sequence
<220> FEATURE:
<223> OTHER INFORMATION: Pep-WH-12 peptide

<400> SEQUENCE: 12

Ala Leu Thr Ser Lys Leu Arg Phe
1               5

<210> SEQ ID NO 13
<211> LENGTH: 20
<212> TYPE: DNA
<213> ORGANISM: Artificial Sequence
<220> FEATURE:
<223> OTHER INFORMATION: TNF-a forward primer

<400> SEQUENCE: 13
ctatctggga ggggtcttcc                                              20

<210> SEQ ID NO 14
<211> LENGTH: 19
```

```
<212> TYPE: DNA
<213> ORGANISM: Artificial Sequence
<220> FEATURE:
<223> OTHER INFORMATION: TNF-a reverse primer

<400> SEQUENCE: 14
atgttcgtcc tgctcacag                                          19

<210> SEQ ID NO 15
<211> LENGTH: 21
<212> TYPE: DNA
<213> ORGANISM: Artificial Sequence
<220> FEATURE:
<223> OTHER INFORMATION: GAPDH forward primer

<400> SEQUENCE: 15
agggctgctt ttaactctgg t                                       21

<210> SEQ ID NO 16
<211> LENGTH: 21
<212> TYPE: DNA
<213> ORGANISM: Artificial Sequence
<220> FEATURE:
<223> OTHER INFORMATION: GAPDH reverse primer

<400> SEQUENCE: 16
ccccacttga ttttggaggg a                                       21
```